United States Patent
Heidari et al.

(10) Patent No.: US 11,419,499 B2
(45) Date of Patent: Aug. 23, 2022

(54) OPTICAL COHERENCE TOMOGRAPHY FOR CANCER SCREENING AND TRIAGE

(71) Applicant: The Regents of the University of California, Oakland, CA (US)

(72) Inventors: Andrew Emon Heidari, Irvine, CA (US); Zhongping Chen, Irvine, CA (US); Bryan S. Benn, Orange, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 885 days.

(21) Appl. No.: 16/253,963

(22) Filed: Jan. 22, 2019

(65) Prior Publication Data

US 2019/0223728 A1 Jul. 25, 2019

Related U.S. Application Data

(60) Provisional application No. 62/619,537, filed on Jan. 19, 2018.

(51) Int. Cl.
*A61B 5/00* (2006.01)
*G01B 9/02* (2022.01)
(Continued)

(52) U.S. Cl.
CPC .......... *A61B 5/0066* (2013.01); *A61B 5/0088* (2013.01); *A61B 5/4552* (2013.01); *A61B 5/7267* (2013.01); *G01B 9/0205* (2013.01); *G01B 9/02091* (2013.01); *G06K 9/00* (2013.01); *G06T 7/0012* (2013.01); *G06T 7/13* (2017.01); *G06T 7/50* (2017.01); *G06T 2207/10068* (2013.01); *G06T 2207/30108* (2013.01)

(58) Field of Classification Search
CPC ... A61B 5/0066; A61B 5/0088; A61B 5/4552; A61B 5/7267; G01B 9/0205; G01B 9/02091; G06K 2209/05; G06K 9/00; G06K 9/6267; G06T 2207/10068; G06T 2207/20084; G06T 2207/30108; G06T 7/0012; G06T 7/13; G06T 7/50; G16H 50/70
See application file for complete search history.

(56) References Cited

U.S. PATENT DOCUMENTS 10,016,185 B2 * 7/2018 Tehrani .............. A61B 17/3403
2010/0330611 A1 * 12/2010 Mycek ................ A61B 5/7264
435/29

(Continued)

OTHER PUBLICATIONS

Xie et al. "GRIN lens rod based probe for endoscopic spectral domain optical coherence tomography with fast dynamic focus tracking" Optics Express. Apr. 17, 2006 / vol. 14, No. 8.

*Primary Examiner* — Mark D Remaly
(74) *Attorney, Agent, or Firm* — Nguyen Tarbet LLC

(57) ABSTRACT

A device for cancer screening and triage using an optical coherence tomography (OCT) imaging system integrated with optical imaging probe is provided. Endoscopic OCT images are generated using the OCT system having a helical probe. The images are further analyzed to generate a depth resolved intensity OCT signal to classify the region of tissue into variable grades of dysplasia to guide the physician's biopsy or resection.

20 Claims, 22 Drawing Sheets
(15 of 22 Drawing Sheet(s) Filed in Color)

(51) Int. Cl.
  *G06T 7/13* (2017.01)
  *G06T 7/50* (2017.01)
  *G01B 9/02091* (2022.01)
  *G06K 9/00* (2022.01)
  *G06T 7/00* (2017.01)

(56) References Cited

U.S. PATENT DOCUMENTS

2012/0245473 A1* 9/2012 Mycek ................. G01N 21/474
                                                          600/479
2019/0231249 A1* 8/2019 Dascalu ................. A61B 5/746
2019/0336063 A1* 11/2019 Dascalu ............... A61B 5/7267

* cited by examiner

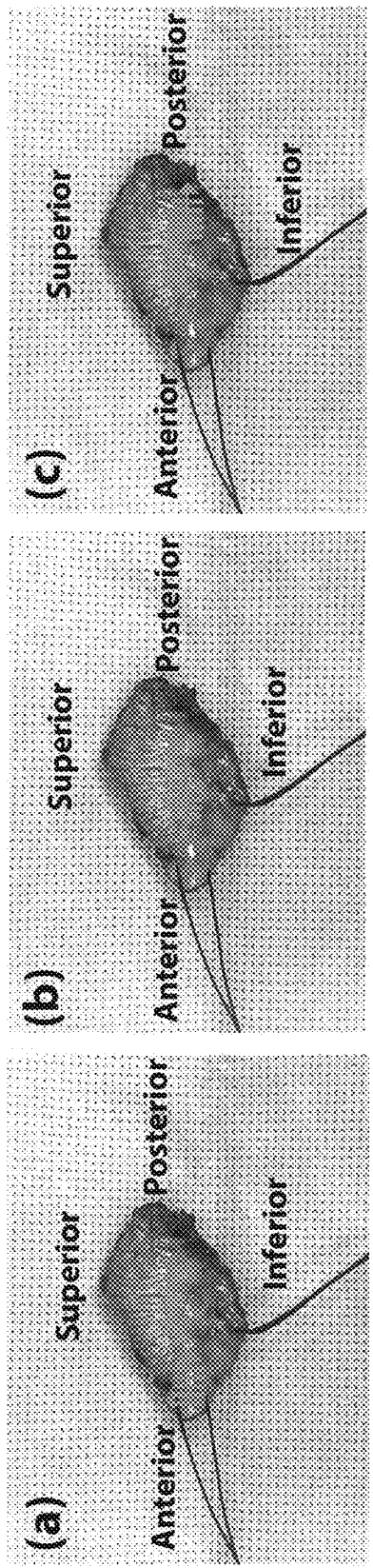
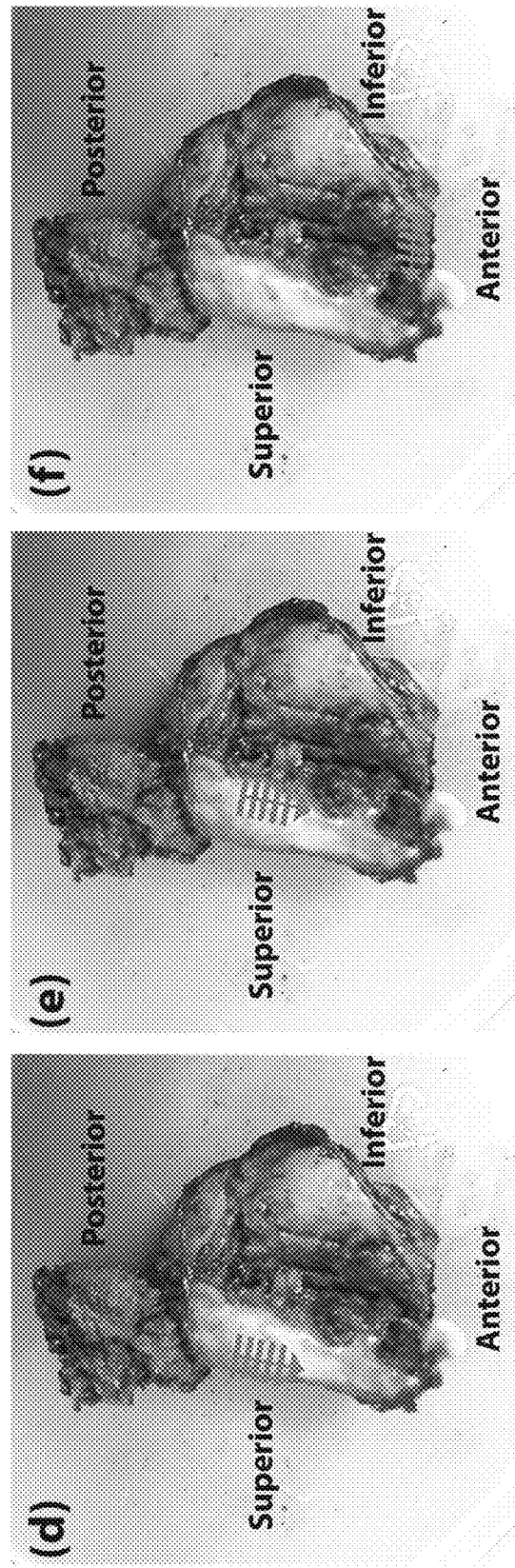
FIG. 17A  FIG. 17B  FIG. 17C
FIG. 17D  FIG. 17E  FIG. 17F

OPTICAL COHERENCE TOMOGRAPHY FOR CANCER SCREENING AND TRIAGE

CROSS-REFERENCES TO RELATED APPLICATIONS

This application is a non-provisional and claims benefit of Provisional U.S. Patent Application No. 62/619,537, filed Jan. 19, 2018, the specifications of which are incorporated herein in their entirety by reference.

FIELD OF THE INVENTION

The present invention relates to a device and a method for cancer screening and triage using an optical coherence tomography imaging system integrated with a side viewing fiber-optic probe and/or a forward viewing optical probe.

BACKGROUND OF THE INVENTION

Screening is an effective way to identify early stage cancer, such as oral squamous cell carcinoma (OSCC), and pulmonary cancer, to reduce its morbidity and mortality, for example. Cancer screening procedures that are fast, reliable, and less invasive are desired for improving diagnostic capabilities. As an example, oral squamous cell carcinoma (OSCC) ranks as the sixth most common cancer worldwide, accounting for approximately 400,000 new cancer cases annually. The high morbidity and mortality of OSCC are attributed primarily to late diagnosis, with more than two thirds of OSCC cases diagnosed at loco-regionally advanced states. Prognosis of OSCC is stage dependent, with an average five-year disease-free survival rate of 80-90% if diagnosed at stage I and II and only 20% if diagnosed at stage III and IV. Thus, early detection and prompt treatment offer the greatest hope to patients with oral cancer, providing the best chance of minimally invasive treatment and better disease outcomes.

Oral cancer is frequently preceded by oral potentially malignant lesions (OPML) which typically present as red, white or speckled lesions. The mechanism of malignant transformation remains unclear, and there are no clear prognostic markers informing on risk in individual patients or to guide the specialist's treatment plan. Therefore, patients with OPMLs require frequent and careful monitoring to ensure early detection of malignant transformation. Currently, monitoring is performed by visual examination and incisional/excisional biopsy. The diagnostic accuracy of visual examination is unreliable, and biopsies have poor patient compliance, requiring specialist skills as well as laboratory facilities that are typically limited to high-resource environments and can be expensive. The key challenge to reducing the mortality and morbidity of OSCC is to generate strategies to identify and detect OSCC at an early stage, and to develop a non-surgical means of monitoring lesions that are at risk of malignant transformation. By overcoming this barrier OSCC outcomes will improve considerably. In low and middle-income countries (LMICs) this need is particularly urgent in remote areas due to the very limited availability of oral cancer specialists.

As another example, pulmonary nodules found on screening or diagnostic imaging studies warrant further evaluation as the potential for newly discovered lung malignancy exists, with implications for drastically changing patient quality and quantity of life. Further evaluation necessitates serial imaging studies, minimally invasive diagnostic lung biopsies, or invasive exploratory surgery. During both lung biopsies and surgical evaluation, potentially cancerous cells and tissues are assessed by visible light bronchoscopy if the lesion is directly visible in the airway, direct palpation is conducted if the nodule is solid and large enough to be grasped, and fine needle tissue aspiration or frozen section during biopsy or dissection. Such methods of cell and tissue assessment are both invasive and time consuming, with no prebiopsy or preresection ability to further risk stratify the likely of the lesion being cancerous.

Visible light bronchoscopy and direct lung tissue palpation are limited in specificity and sensitivity to differentiate between normal lung parenchyma and severe dysplasia or carcinoma in situ due to limited contrast between such lesions when assessed by these methods. The background and experience of the operative physician may also yield variable interpretations of both physical palpation and bronchoscopic view of the lesion in question.

In some cases, small portions of the tissue are dissected using fine needle tissue aspiration or frozen sectioned during biopsy, and further analyzed. Tissue and cellular analysis post procedure with histopathological embedding, sectioning, and staining represents the gold standard to provide cellular level assessment of the presence and specific type of cancer. Unfortunately, specimen acquisition is not only invasive, but also quite time consuming. During diagnostic procedures, physicians will utilize frozen tissue sectioning or fine needle aspirate staining to obtain a general idea of both diagnosis and spread of disease. This process is similarly invasive and does not yield a comprehensive view of the target lesion, potentially missing cancer cells.

The present invention may allow for a 3D-helical scanned optical coherence tomography imaging system with diagnostic methods that provides a better understanding of the tissue sub-structure. The OCT images generated and processed using the present invention may be used by physicians to clearly identify different specific areas within the suspicious tissue due to the variable tissue stratification between healthy, dysplastic, and cancerous mucosa. This information may be used by a physician when planning both the initial biopsy and subsequent surgical resection. The diagnostic methods may be faster and less invasive than the standard frozen tissue biopsy, for example, thus decreasing patient risk from additional invasive biopsies and anesthesia time.

Non-invasive imaging modalities such as: optical coherence tomography (OCT), auto-fluorescence imaging, confocal microscopy, narrow band imaging (NBI), and Raman spectroscopy may aid in the non-invasive assessment of tumor margins. These technologies are rapid and also could potentially be used in situ as well as in specimens that have been freshly resected. Of the aforementioned imaging modalities, OCT is unique in that it provides near histopathological resolution cross-sectional images of tissues in real time, a desirable aspect of a tool developed for intraoperative use. OCT uses differences in tissue optical properties (chiefly optical scattering) to generate tissue contrast. Contrast does not: 1) depend upon biochemical absorbers such as in fluorescence imaging; 2) require the use of dyes, stains; and 3) does not require special modification of operating room ambient lighting such as in many fluorescent techniques. OCT has been shown to differentiate normal and abnormal oral mucosa5,2. However, direct subjective interpretation of OCT images by human observers requires extensive cumbersome training 6. Since contemporary OCT systems may acquire up to 40 images/second, this massive amount of data poses a challenge for clinical implementation.

Deep learning, a subfield of machine learning leverages the structure of neural network to learn how to classify data. Deep learning methods have found widespread use across fields such as bioinformatics, healthcare and image recognition for skin cancer diagnosis. A neural network is comprised of a series of neural layers that are further comprised of neurons. In the circumstance of a convolutional neural network each neuron. A neuron holds a value called an activation that dictates Supervised learning, a deep learning methodology, trains a layered network to classify input data based on its labels. As labeled data is progressively fed into the network the network improves its classification ability through adjusting weights located at each neuron to minimize the error of the classifications. Convolutional neural networks (CNN), a type of network trained commonly through a supervised learning method is capable of differentiating images based upon their abstraction by convolution filters. A convolutional filter is used to condense data in each kernel or sub-matrix of an image through element matrix multiplication and summation. Through such processes specific convolutional filters can be designed to extract classifying characteristics of 2-D image data. This invention utilizes a CNN to rapidly classify 3-D OCT images of oral mucosa in order to differentiate normal and abnormal tissues specifically pertaining to head and neck squamous cell carcinoma (HNSCC) and generate an immediate classification.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

In some aspects, the present invention features an optical coherence tomography (OCT) imaging system integrated with an imaging probe that provides a better understanding of the tissue substructure to screen for cancerous tissue in real time. This OCT imaging system utilizes a continuously learning convolutional neural network (CNN) to provide rapid classifications which can guide a physician during an examination. The CNN is trained on a remote server using a pre-existing sample training set with tissue sample images known to be healthy or malignant. The weights of the network thus trained can then be transmitted to the OCT device, which can then generate a classification while reading images in-situ at the frame rate of the OCT device. In some cases, a GPU processor may be needed to process the images quickly enough. The OCT device may communicate with the processor via a wireless link. After samples are taken and biopsies the classifications may be sent back to the remote server, so they can be added to the training data set and the weights of the network updated. The updated weights can then be retransmitted to all users, allowing the network to continuously learn.

One of the novel features which allows for rapid classification using the continuously learning convolutional neural network is that the system includes a means for observing the sample region being scanned at the time of each imaging frame. In some embodiments, this means for observing the sample region may comprise a camera, a magnetic tracker, MEMS based positioning, or an IR tracker. This feature importantly allows for the co-registration and orientation of the imaging frames. This co-registration and orientation of the imaging frames significantly allows for a precise co-registration of the gold standard histopathology and the imaging frame. In turn, this greatly aids and improves the sensitivity and specificity of a classification network.

One of the technical features of the present invention is the integration of gradient refractive index (GRIN) rod lens for imaging for acquiring image data from inside an oral cavity, for example, and analyzing the image to obtain tissue stratification. In one example, the tissue stratification is used to identify of the tissue is healthy, dysplastic or malignant. Using GRIN rod lenses in the OCT imaging systems typically causes unwanted spherical and/or chromatic aberrations. In addition, the use of a long piece of glass such as the GRIN rod will cause dispersion between the probe sample arm and reference arm in the OCT system. This will result in a widening of the point spread function in the OCT signal, effectively reducing the resolution. To account for such dispersion with hardware modifications, an equal length of glass or water cuvette may need to be placed in the optical path of the reference arm of the OCT interferometer. This is an inconvenience in optical design. The inventors have recognized these issues and incorporated image correction techniques that correct the aberrations. As an example, the image correction techniques include a flattening process. Herein, a top surface contour of the OCT image is identified by a surface tracing dynamic programming algorithm. The surface position and the data found underneath are flattened to standardize the size of the image data set. By flattening the OCT image, aberrations caused by the GRIN rod may be reduced. In addition, flattening the image results in a reduced dimensionality of the image, which increases the processing speeds, thereby making it possible to screen the tissue for cancer in real time.

Without wishing to limit the invention to any theory or mechanism, it is believed that the technical feature of the present invention advantageously provides for real time, low cost, and non-invasive imaging system. None of the presently known prior references or work has the unique inventive technical feature of the present invention.

BRIEF DESCRIPTION OF THE DRAWINGS

This patent application contains at least one drawing executed in color. Copies of this patent or patent application publication with color drawings will be provided by the Office upon request and payment of the necessary fee.

The features and advantages of the present invention will become apparent from a consideration of the following detailed description presented in connection with the accompanying drawings in which:

FIGS. 17A-F show photographs of representative tissue sample areas imaged for two of the 6 head and neck cancer cases. The parallel bars indicate area scanned. (FIGS. A-C): Series of 3-D OCT volumes acquired from anterior to posterior aspect of the tongue glossectomy main specimen. (FIGS. D-F): Series of 3-D OCT volumes acquired for the superior and anterior aspect of the composite head and neck resection.

FIGS. 19A-C: Labeled and orientated visible light images of a hemiglossectomy main specimen scanned with 3-D OCT. OCT scanned area show with the parallel bars. Scan direction follows the intersecting arrow. FIGS. 19D-F: Corresponding H&E stained histology sections FIGS. 19G-I: CNN classification of the scanned area indicated in FIGS. 19A-C With the Z axis as the classified probability and the X axis as the B-Scan number out of 1000 total B-scans in a single OCT-3D volumetric data acquisition.

DESCRIPTION OF PREFERRED EMBODIMENTS

Figure 1A:
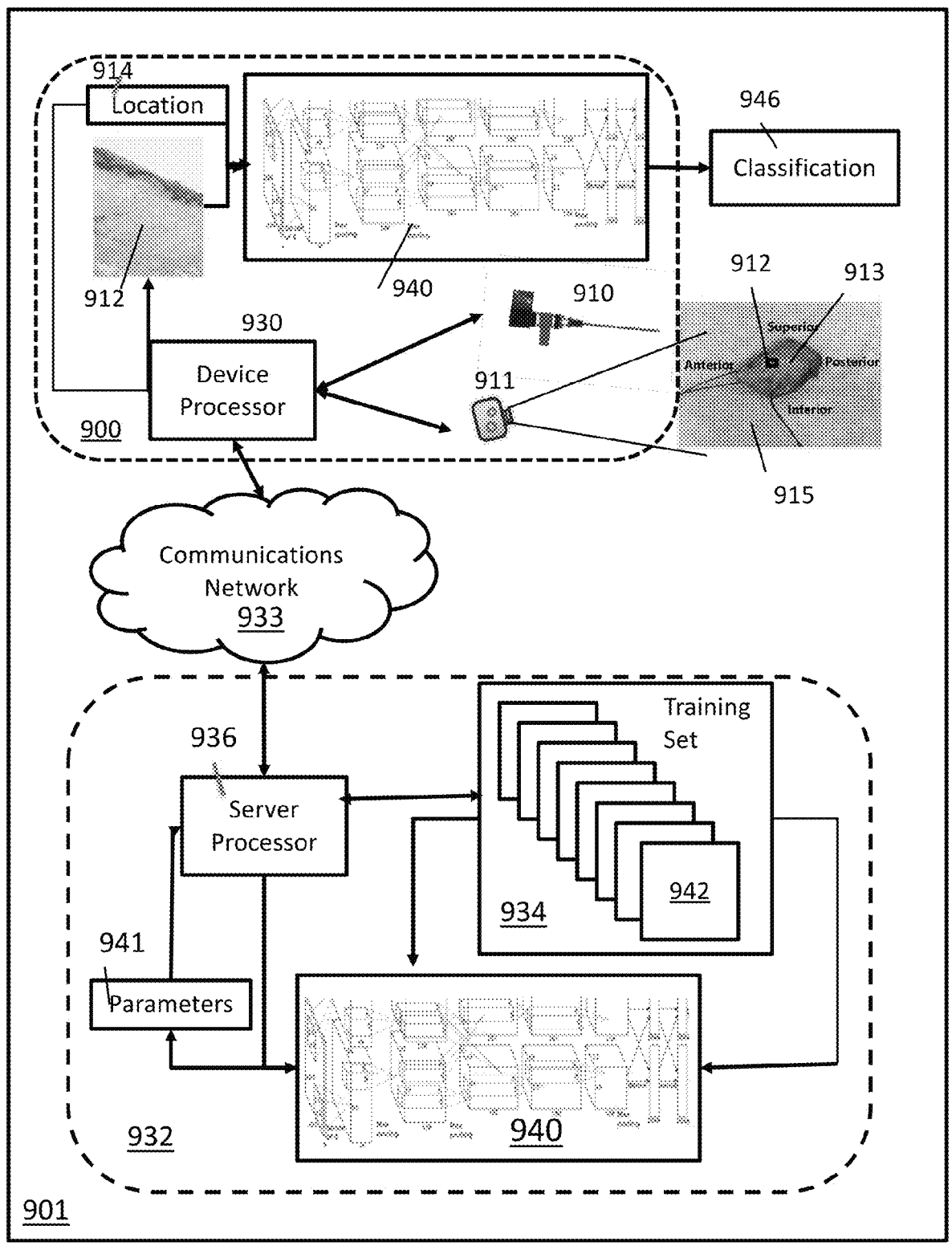
FIG. 1A shows a diagram of the system of the present invention, comprising a screening device and a deep learning server.
Figure 1B:
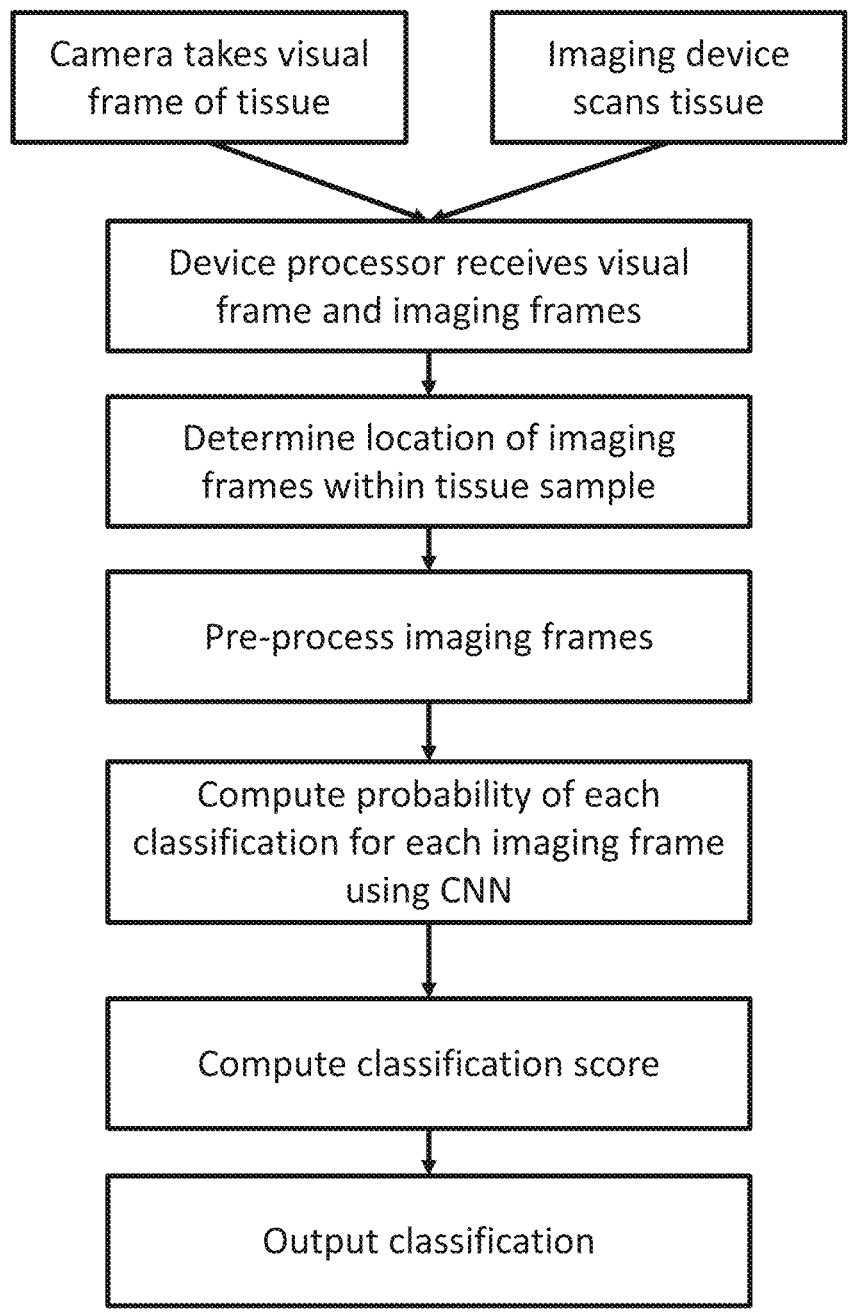
FIG. 1B shows a process flow for the screening device.
Figure 1C:
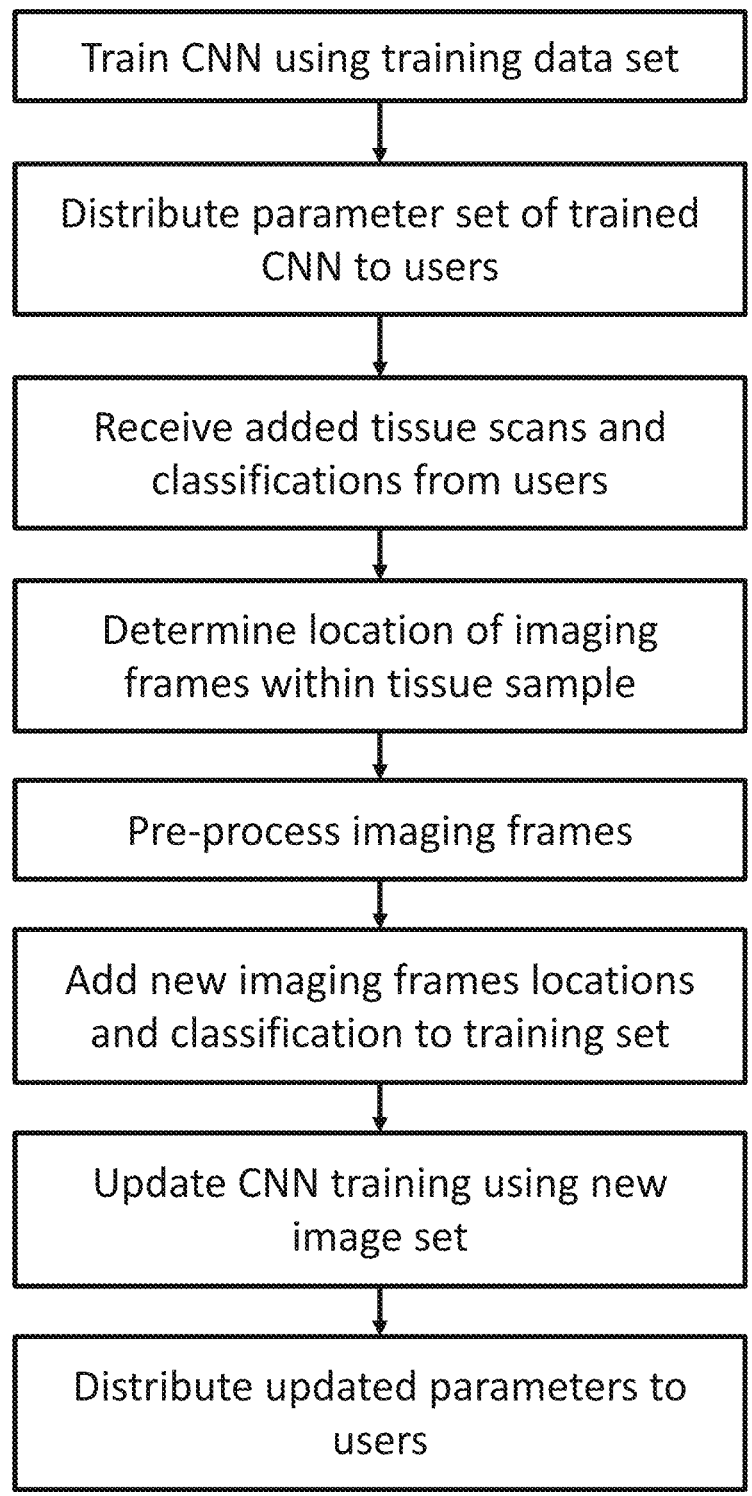
FIG. 1C shows a process flow for the server.
Figure 2:
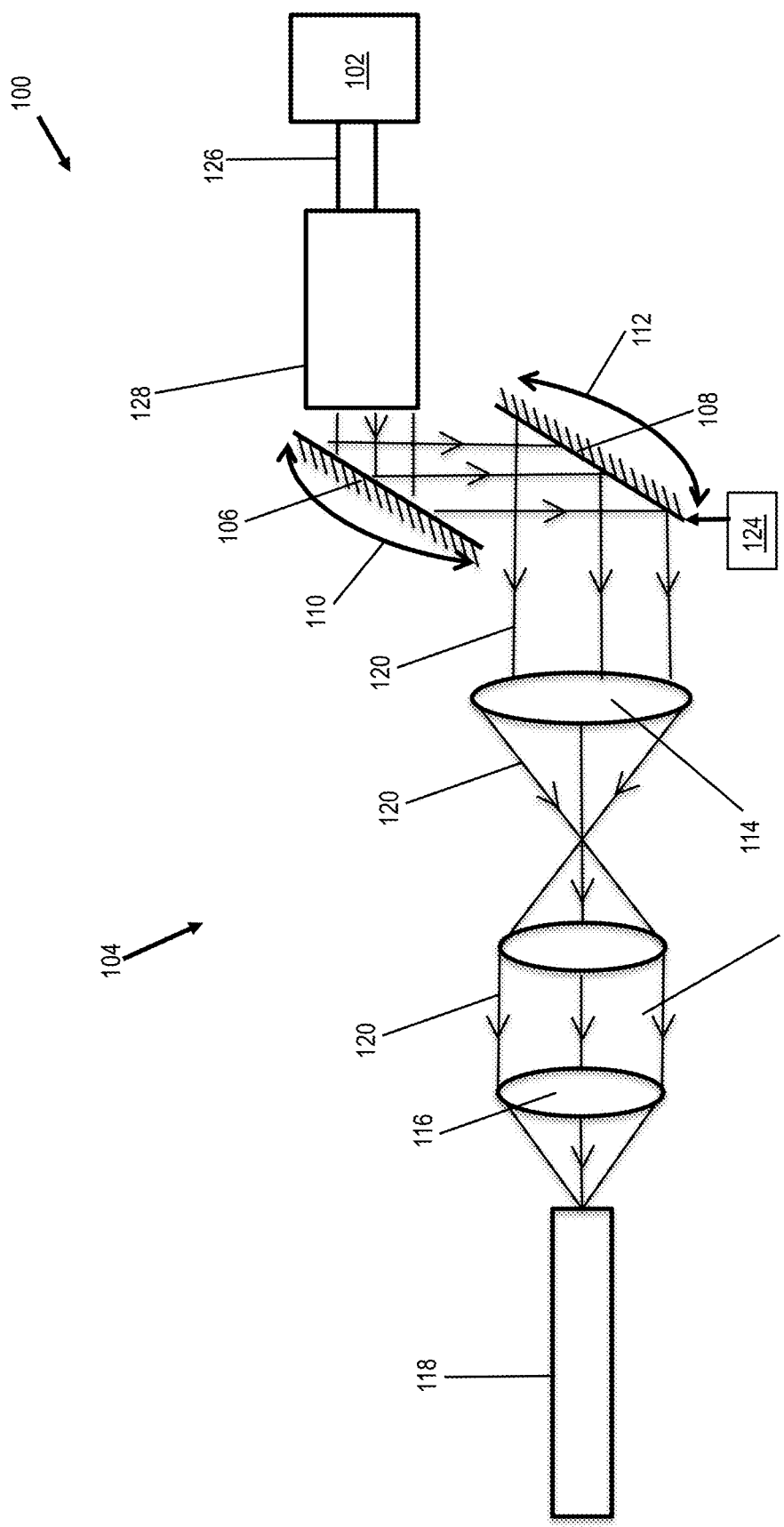
FIG. 2 shows an exemplary schematic view of a gradient refractive index (GRIN) rod probe of an optical coherence tomography (OCT) imaging system.

Following is a list of elements corresponding to a particular element referred to herein:
- 100 OCT imaging system
- 102 optical system
- 104 imaging probe
- 106 X-axis galvanic mirror
- 108 Y-axis galvanic mirror
- 110 arrow
- 112 arrow
- 114 beam reduction relay optics
- 116 objective lens
- 118 GRIN rod lens
- 120 arrow
- 124 digital to analog converter
- 126 fiber optic connection
- 128 fiber optic collimator
- 202 optical source
- 203 beam splitter
- 204 sample beam
- 206 reference beam
- 208 sample arm
- 210 reference arm
- 212 reflection
- 214 reflection
- 216 balanced detection
- 220 processor
- 300 side view
- 302 rail
- 400 example embodiment
- 404 biological tissue
- 406 imaging probe
- 412 linear translation stage
- 414 fiber optic rotary joint
- 416 brushless DC motor
- 418 fiber
- 422 arrow
- 500 example design
- 502 fiber core
- 506 coreless fiber
- 508 focusing fiber
- 514 angle cleaved portion
- 516 cone
- 702 OCT image
- 704 flattened image
- 706 plot
- 802 OCT image
- 804 OCT image
- 806 OCT image
- 808 plot
- 810 plot
- 812 plot
- 900 screening device
- 901 classification system
- 910 imaging device
- 911 camera
- 912 imaging frames
- 916 depth resolved intensity distribution
- 930 device processor
- 932 server
- 933 communications network
- 936 server processor
- 940 supervised learning algorithm
- 941 parameters
- 942 training data set 943 sample images
944 neural network
945 layers
946 classifications
1001 multi-lumen guide catheter
1002 OCT fiber
1003 biopsy needle
1004 tissue sample
1101 mirror
1102 objective lens
1103 GRIN rod
1104 sample
1105 fiber optic collimator
1106 reference light
1107 light reflected by the sample Referring to FIG. 1A-1C, in one embodiment the invention may comprise a device (900) for in-situ or in-vivo tissue cancer screening, capable of classifying observed tissue in real time. The device (900) may comprise an imaging device (910) capable of scanning a tissue sample, the imaging device (910) configured to generate imaging frames (912) of a tissue sample (913) at a periodic time interval (918), wherein the imaging frames comprise a scan across the tissue sample, a camera (911), disposed to observe the area of the sample being scanned by the imaging device, the camera (911) capable of generating a camera image of the sample (913), wherein the camera image comprises a reference frame, an output device, and a device processor (930), operationally connected to the imaging device (910), the camera (911) and the output device. In other embodiments, the device may comprise a means other than a camera for observing the sample region being scanned at the time of each imaging frame. As non-limiting examples of other means for observing the sample region being scanned, the means may comprise a magnetic tracker, MEMS based position sensor, an IR tracker, an IR LED with an IR camera, a physical positioning tracker, or a probe motor positioning tracker.

In some embodiments, other mechanisms may be used to obtain the location of the scanned imaging frames with respect to the tissue sample, such as a magnetic tracker, an IR camera and IR LEDs illuminating the area of the tissue. In some embodiments the problem could be equipped with sensors capable of measuring the probes position.

In some embodiments, the device processor (930) may be configured to execute computer-readable instructions. As a non-limiting example, the instructions may comprise receiving a plurality of imaging frames (912) from the imaging device (910), receiving a camera image (914) from the camera (911), identifying the position of the imaging frames (915) within the reference frame of the camera image (914), pre-processing the image frames (912) to prepare them for classification, using a pre-trained supervised learning algorithm (940) to classify the image frames (912) within a plurality of classifications, and reporting the classification (946) of the image frame to a user using the output device (920).

In some embodiments, the supervised learning algorithm may take as inputs the positions of the imaging frames within the camera image, and the imaging frames, and produce as an output a classification (946). The device processor (930) may be capable of generating the classification (946) within the periodic time interval (918) of the imaging device (910), so as to enable the physician to use the device in real-time while scanning tissue in-vivo.

In some embodiments, the classifications (946) may comprise a healthy class and a malignant class. In other embodiments, the supervised learning algorithm (940) may have been trained on a training data set (942) comprising sample images (943) of tissue with known classifications (946). In some embodiments, the supervised learning algorithm (940) is a convolutional neural network (944). In some other embodiments, the periodic time interval (918) of the imaging device (910) and the time the processor (930) takes to classify the image frame (912) at each time interval may be one second or less.

In some embodiments, pre-processing the image frame (912) to prepare it for classification may comprise determining an edge (913) of the image (912), flattening the image (912) based on the edge (913), normalizing and scaling the intensity of the image, selecting a region of interest (ROI) (914) of the flattened image (912); and generating a depth resolved intensity distribution (916) of the ROI (914).

In some embodiments the invention features a system (901) for generating in-situ or in-vivo classifications of tissue-samples in real time. As a non-limiting example, the system (901) may comprise a remote screening device (900), and a server (932), the server (932) capable of communicating with a server over a communications network. In some embodiments, the remote screening device may be the device described above. According to some embodiments, the server (932) may comprise a memory, capable of storing computer readable instructions, a set of training data (942) comprising a plurality of sets of sample images (943) of tissue samples (913), the locations of the sample images relative to others in the same set, and predetermined classifications (946), wherein each set of sample images comprises a set of images of a single tissue sample and a plurality of parameters (941). In further embodiments, the server may further comprise an input mechanism, comprising means for a user to upload additional sets of images to the server, and a server processor (936), configured to execute computer readable instructions. As a non-limiting example, the computer readable instructions may comprise, training the supervised learning algorithm (940) using the training data set (942) to classify images of tissue samples (912), wherein training comprises adjusting the plurality of parameters (941) so as to minimize a cost function, wherein the cost function is a function of the number of incorrect classifications output by the algorithm for a subset of the training data set, receiving sets of images (912) from the input mechanism, their locations within a common reference frame, and classifications (946), adding the received sets of images (912), locations, and classifications (946) to the training data set (942), updating the training of the supervised learning algorithm (940), comprising updating the plurality of parameters (941); and transmitting the updated plurality of parameters (941) to the remote device (900).

Figure 21:
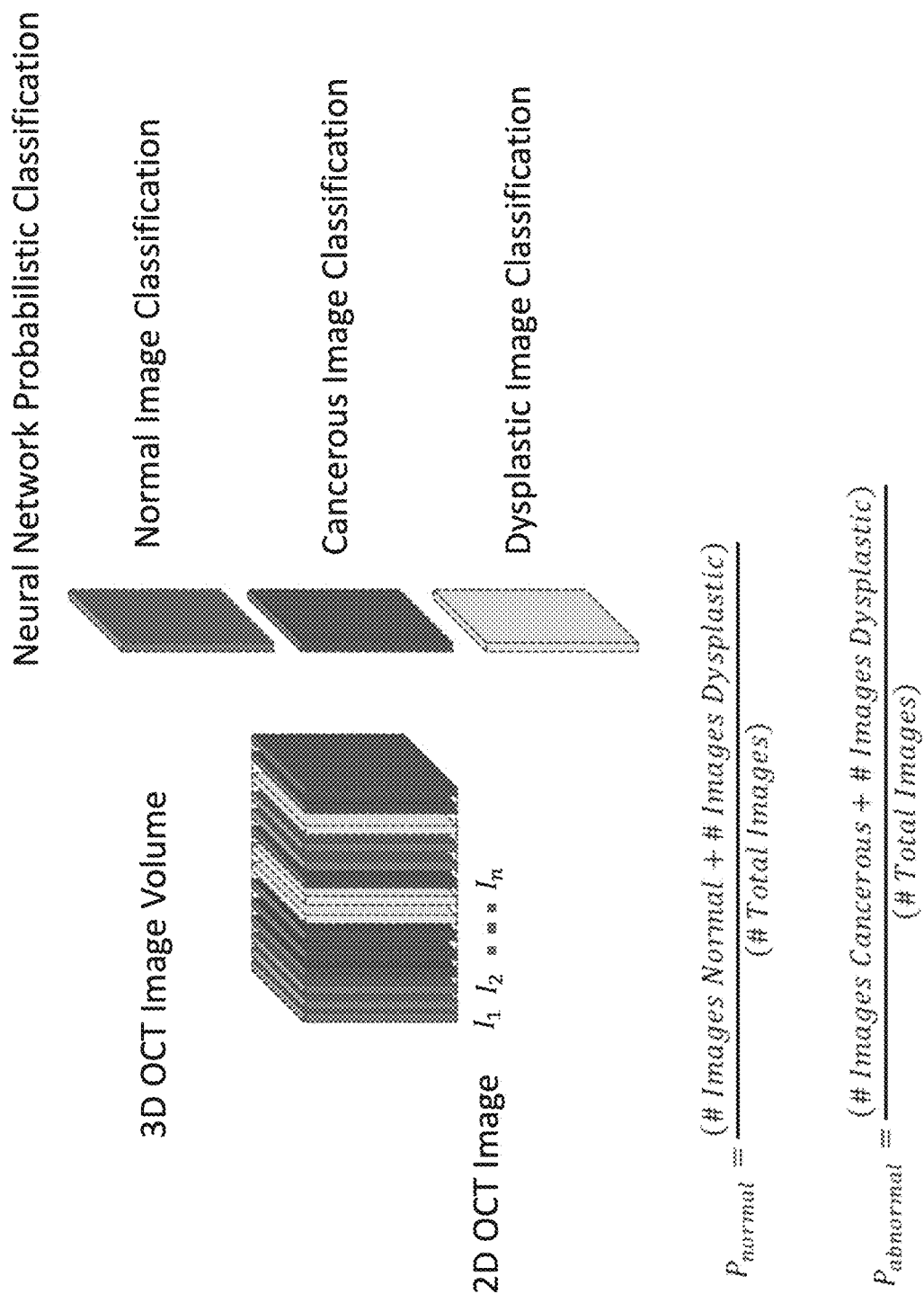
FIG. 21 shows an illustration of the classification of healthy or cancerous images.

In one embodiment, the device and server processors may comprise at least one multi-core processors such as a graphic processing unit (GPU). In some embodiments, the training data set may be constructed by determining a classification for a subset of imaging frames in a scan and extrapolating the classification of nearby imaging frames in the same set. FIG. 21 details the implementation of the assumption made for healthy or cancerous image classification. After the neural network has sufficiently trained on a large OCT data set and correlative gold standard histopathological slices, it is used to classify unknown OCT images of biological tissue. As shown in FIG. 21, the neural network will classify all the images in a given 3D acquisition volume denoted individually by red, yellow and blue 2D image segments corresponding to cancerous, dysplastic or healthy classifications. Based on the number of images identified for each respective category, a probability is calculated per Equation 1. This probability is the output of the system that can inform health care workers what the involvement of the tissue could be.

In some other embodiments, pre-processing the image frame (912) to prepare it for classification may comprise: determining an edge (913) of the image (912); flattening the image (912) based on the edge (913); normalizing and scaling the intensity of the image; selecting a region of interest (ROI) (914) of the flattened image (912); and generating a depth resolved intensity distribution (916) of the ROI (914).

According to an embodiment, the server (932) may be implemented in a cloud computing architecture. According to another embodiment, the imaging device (910) may be an optical coherence tomography device comprising: an optical imaging light source (202); a beam splitter (203); a fiber optic collimator (128) configured to collimate a light beam from the source (202); a gradient refractive index (GRIN) rod lens (118), capable of reflecting light outwards from the probe into surrounding tissue, optically connected to the fiber optic collimator (128), wherein the collimated light beam from the fiber optic collimator is directed into the GRIN rod lens; and a detector, optically connected to the gradient refractive index rod lens and to the optical imaging light source, capable of generating optical coherence tomography (OCT) images via interferometry.

In some embodiments, the imaging device may be an auto-fluorescence imaging device, a confocal microscopy device, a narrow band imaging (NBI) device, an optical coherence tomography device or a Raman spectroscopy device. As a non-limiting example, the imaging device may be an optical coherence tomography device, comprising: an optical imaging light source (202); a beam splitter; a fiber optic collimator (128) configured to collimate light from the source (202); a fiber optic rotary joint (414) operative coupled to a fiber (418), the fiber optic rotary joint configured to rotate the fiber (418) inside the tissue; the fiber, having an angle cleaved portion, capable of focusing and directing light into the surrounding tissue; and a detector, optically connected to the light source and the fiber.

In one embodiment, the system may further comprise a set of galvanic mirrors (106, 108), disposed to direct light from the collimator into the GRIN rod lens. As a non-limiting example, the set of galvanic mirrors (106, 108) may include an X-axis galvanic mirror (106) configured to scan the light beam in a longitudinal direction and further includes a Y-axis galvanic mirror (108) configured to scan the light beam in a transverse direction. In another embodiment, the system may further comprise a beam reduction relay optics (114) configured to reduce a diameter of the light beam from the set of galvanic mirrors (106, 108) into an objective lens (116), the objective lens configured to focus the light beam into the GRIN rod lens (118).

In some embodiments, the device may further comprise a fine needle aspiration biopsy needle (1003). In other embodiments, the light beam may be centered at a near-infrared wavelength. In still other embodiments, the system may further comprise a linear translational stage (412) configured to translate the fiber inside the tissue. In yet other embodiments, the source may comprise a vertical cavity surface emitting laser. In an embodiment, the fiber (418) may comprise a cored portion (502) and a coreless portion (506), wherein the coreless comprises a focusing portion (510) and an angle cleaved portion (514) and is configured to adjust a working distance of the fiber (418) from the tissue. In another embodiment, the angle cleaved portion (514) may be coated with gold to increase an internal reflection of the light out of the fiber (418).

Referring now to FIGS. 2-9F, the present invention may feature a device for cancer screening in tissue using a high-speed endoscopic OCT imaging system (100) having an imaging probe (104). In one example embodiment, the imaging probe (104) may be may include a gradient refractive index (GRIN) rod lens (118) that transducts light from an optical source of an optical system (102) (hereafter interchangeably referred to the optical imaging system) into a space/cavity to screen the tissue within the space/cavity for cancerous legions. Light beam from the optical source of the optical system (102) may be coupled to a fiber optic collimator (128) via fiber optic connections (126).

Figure 3:
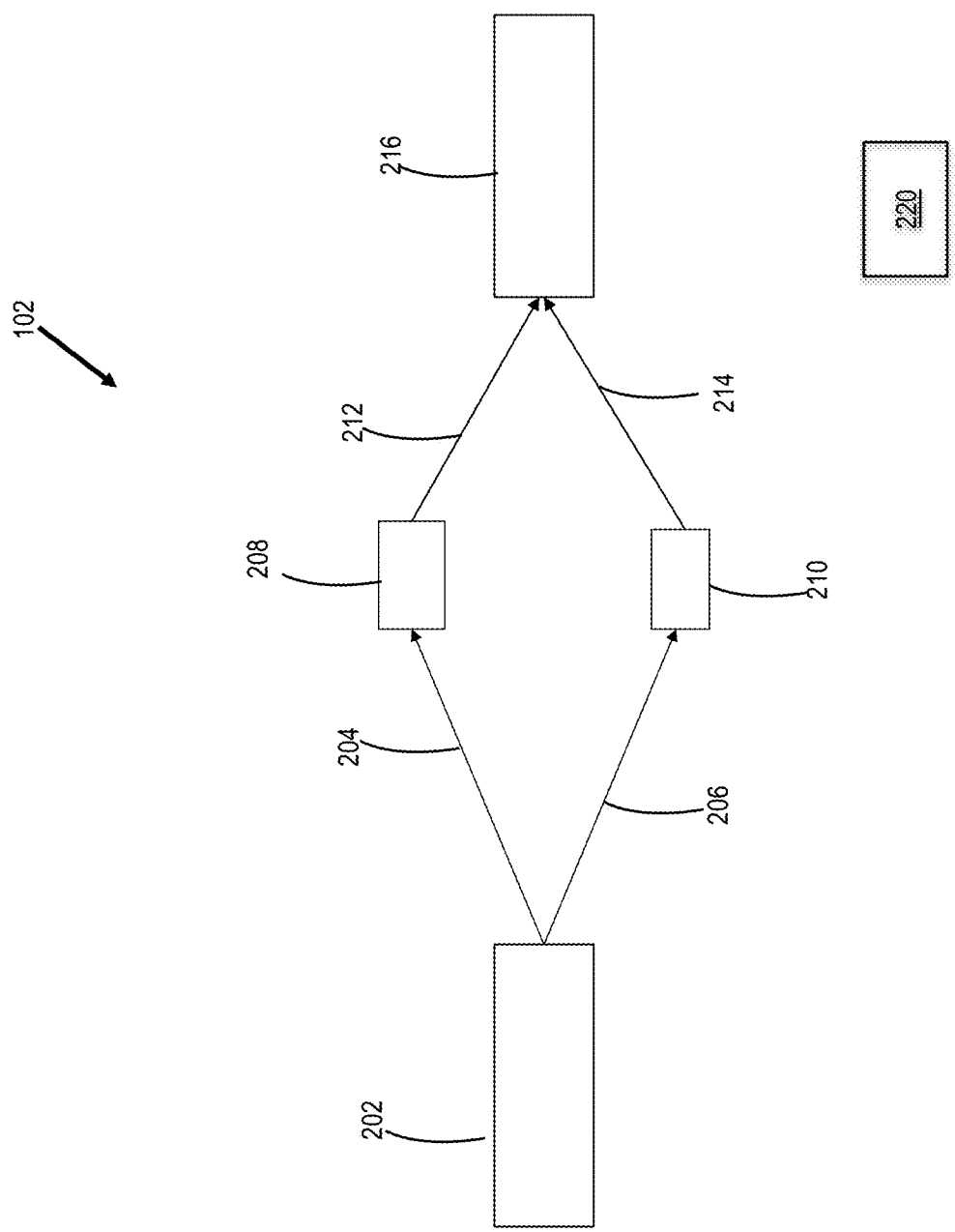
FIG. 3 shows an example OCT imaging system having a low coherent light source.

In some embodiments, the OCT imaging system (100) may include time domain and Fourier domain OCT. In other embodiments, the OCT system may be built based on spectrometer based OCT or a swept source laser or low coherent light source based OCT. A non-limiting example OCT system having a low coherent light source (202) is shown in FIG. 3. Light from a low-coherent light source or optical source or source (202) may be utilized in a Michaelson based interferometer comprising of a static reference arm (210), probe based sample arm (208), and balanced detection (216). Low-coherent light is initially split into a reference beam (206) and sample beam (204) where their reflections (212, 214) are later combined, interfered, and detected by the balanced detection (216) to generate an OCT image. In one non-limiting example, the optical source (202) of the optical system (102) may be a low coherent light source emitting near infra-red wavelengths (e.g., 930 nm). The optical source may include sources such as vertical cavity light emitting lasers (VCSELs), light emitting diodes (LEDs), lasers, and the like. The difference in the distance traveled between the two interference arms will cause shifts in frequency that are captured in the interference fringe pattern. As such, the sample beam (204) is directed into the imaging probe (104) as discussed below.

The light beam or sample beam (204) from the optical system (102) is collimated using the fiber optic collimator (128) and directed towards a set of galvanic mirrors (106, 108). The set of galvanic mirrors (106, 108) may be coated with gold to increase reflectance of the near infra-red wavelengths incident on them. The set of galvanic mirrors may include an X-axis galvanic mirror (106) and a Y-axis galvanic mirror (108) which are voltage controlled high-precision mirrors that steer or scan the light (indicated by arrows 120) in the lateral (X-axis) (indicated by arrow 110) and transverse (Y-axis) direction (indicated by arrow 112). The set of galvanic mirrors (106, 108) may be driven by a waveform generated by a digital to analog converter (124), which in turn may be controlled by a computer (not shown in FIG. 1).

Light from the set of galvanic mirrors (106, 108) is then directed towards a beam reduction relay optics (114) and then focused into the GRIN rod lens using an objective lens (116). The beam reduction relay optics (114) includes a set of lenses that reduces the diameter of the light beam without altering the alignment of the setup. The GRIN rod lens (118) may be a long one pitch GRIN rod that relays light from a proximal portion of the imaging probe (104) to the patient's tissue. In one non-limiting example, the GRIN rod may be over 10 cm long, and 4 mm in diameter. The GRIN rod may be of varying pitch, ranging from an integer multiple of 1*n, 1.25*n, 1.5*n, 1.75*n, and so on, where n is the refractive index at the center of the GRIN rod. In some example embodiments, the GRIN rod may be longer to provide a separation between the clinician and the patient.

From the relationship between frequency and light physical traveled distance, the interference fringe pattern is converted into cross-sectional tomographic images of tissue generated at near histologic resolution with >5 μm depth resolution. The OCT images show the macroscopic characteristics of the epithelial and sub epithelial structures. With an oral mucosal penetration depth of approximately 2 mm, the imaging range of the OCT imaging system with the GRIN rod lens is suitable for interrogating the thin (0.2-1 mm) human oral mucosa, for example. Previous studies using OCT have demonstrated the ability to evaluate macroscopic characteristics of epithelial, sub epithelial, and basement membrane structures and show the potential for near histopathological-level resolution and close correlation with histologic appearance. In this way, the OCT imaging system of the present invention provides an OCT-based diagnostic tool with immediate triage output for diagnosing oral potentially malignant lesions (OPMLs) and oral squamous cell carcinoma (OSCC), for example. Thus, the present invention of the OCT system integrated with the GRIN rod lens probe provides a novel Optical Coherence Tomography (OCT) imaging system to collect baseline normative data for oral tissues that were healthy, dysplastic or malignant. Additionally, the OCT system may include a processor (220) that analyzes the images with increased diagnostic accuracy in a low-cost setting, as discussed further below.

Figure 4:
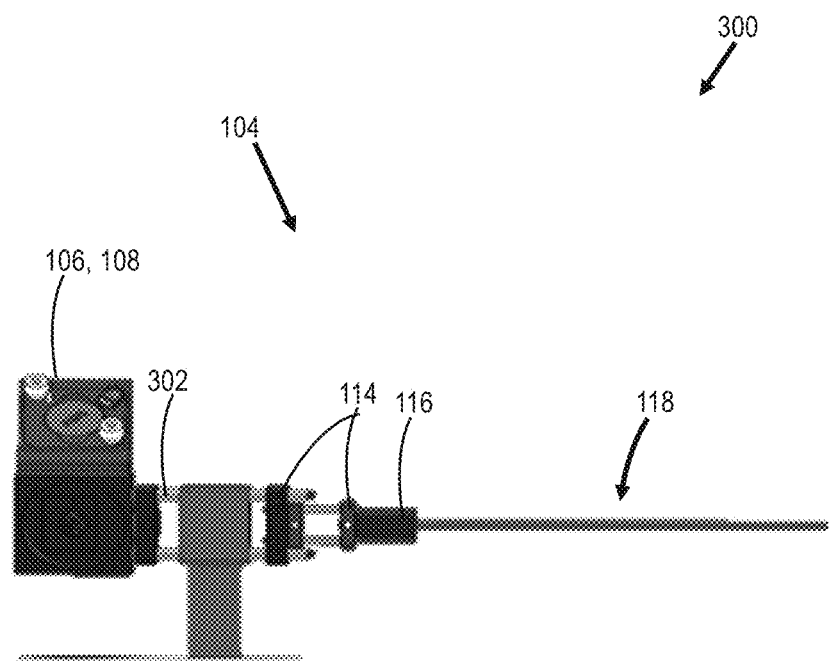
FIG. 4 shows a side view of the GRIN rod probe.

A side view 300 of the imaging probe (104) having the GRIN rod lens (118) is shown in FIG. 4. The optical components including the GRIN rod lens (118), the objective lens (116), and the beam reduction relay optics (114) may be mounted on a rail (302) to maintain the alignment of the optical components during imaging.

Figure 5:
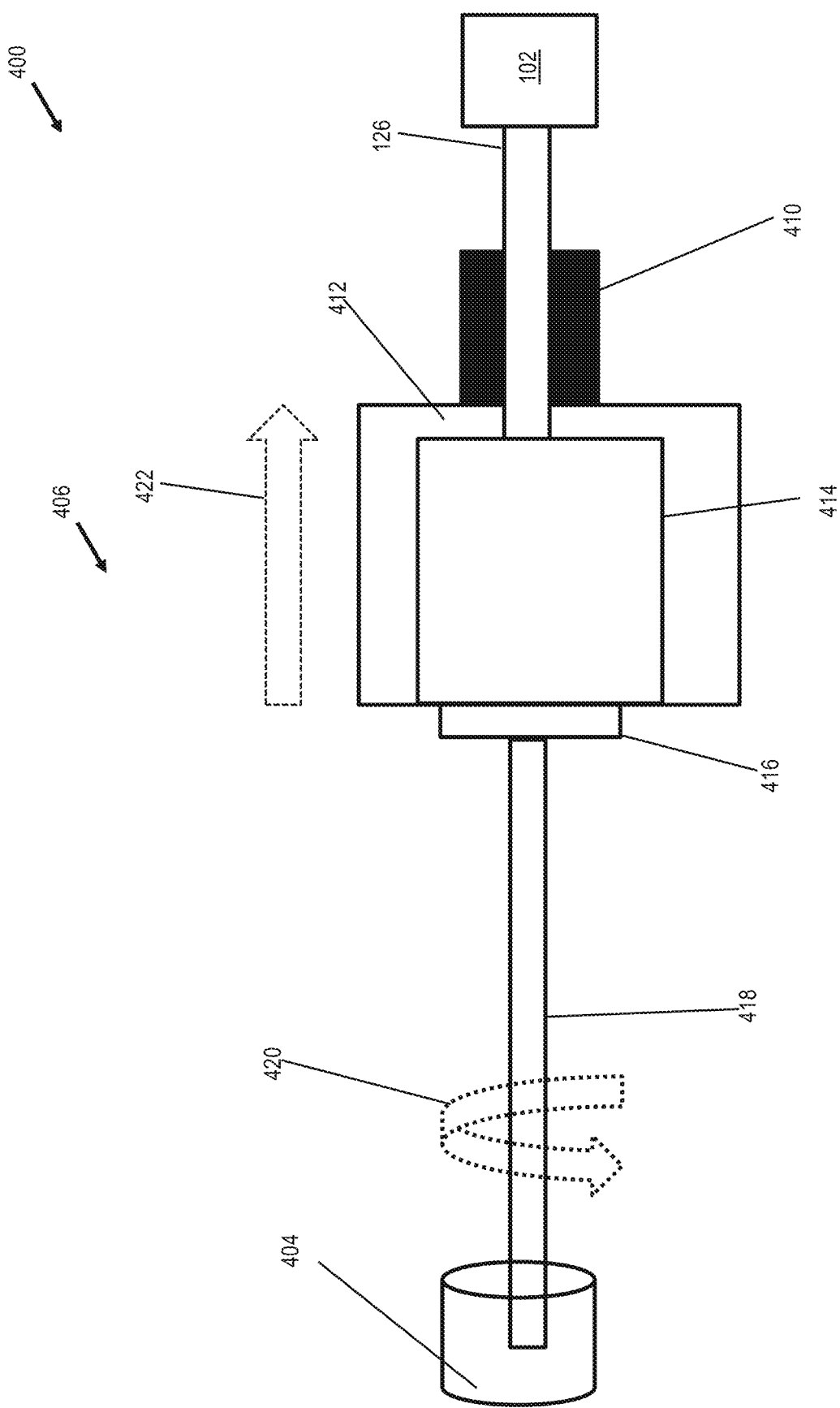
FIG. 5 shows an example embodiment of a helical scanning probe having a fiber.

Turning now to FIG. 5, an example embodiment (400) of an imaging probe (406) is shown. Specifically, the imaging probe (406) may be an endoscopic side viewing helical scanning probe that includes optical and mechanical components that allow for the rotation and translation of the probe (406) inside a biological tissue (404). With the side viewing helical scanning probe (406), the inside of the tubular structure (e.g., patient's airway) of the tissue may be imaged. The optical components of the probe (406) may include a single mode fiber (418), a fiber optic connector, and gold coated, 45-degree polished rod mirror. As explained previously with reference to FIGS. 1 and 2, the light beam from the optical source (202) of the optical system (102) may be coupled to the fiber optic collimator (128) via the fiber optic connections (126).

In some embodiments, the helical scanning probe (406) may include a fiber optic rotatory joint (FORJ) (414), a linear translational stage (412), and a brushless DC motor (416) that transducts light from the optical system (102) to a fiber (418). The FORJ (414) is comprised of a stationary and rotary component. The stationary component houses coupling optics that transduct light into the rotary mated coupling optics. The distal end of the FORJ (414) plugs into the fiber optic probe. Herein, various fiber optic connector interfaces may be used without deviating from the scope of the invention. Some non-limiting examples of interfaces include FC/APC and SC/APC. The interfaces allow for different fiber optic connector terminated imaging probes to be easily plugged into and rotated by the FORJ. The FORJ also has a means of mechanical rotational torque transduction in the form of a gear or belt pully system on the rotary component. The fiber (418) may be driven by and proximally rotated (indicated by arrow 420) by the FORJ (414).

In other embodiments, the helical scanning probe (406) may additionally include mechanical belt and pulley set, triple wound torque coil, and stainless-steel housing for the optical components (not shown in FIG. 5). During image acquisition, the helical scanning probe (406) may be rotated such that a circumferential view of the airway lumen can be obtained. In some example embodiments, the helical scanning probe (406) may be encased in a protective plastic outer layer that may serve as the interface between the tissue and probe. Encapsulating the probe may reduce unwanted shearing contact as well as exposure to bodily moisture or other fluidics that may otherwise damage the probe. In addition, the probe may be coated with gold on the angle cut distal surface to improve the total internal reflection of the light beam radially out of the probe. To obtain 3D volumetric images, the probe may be then linearly translated backward (as indicated by arrow 422) while being rotated (arrow 420). The size and shape of the fiber (418) may be adjusted based on the imaging requirement.

Figure 6:
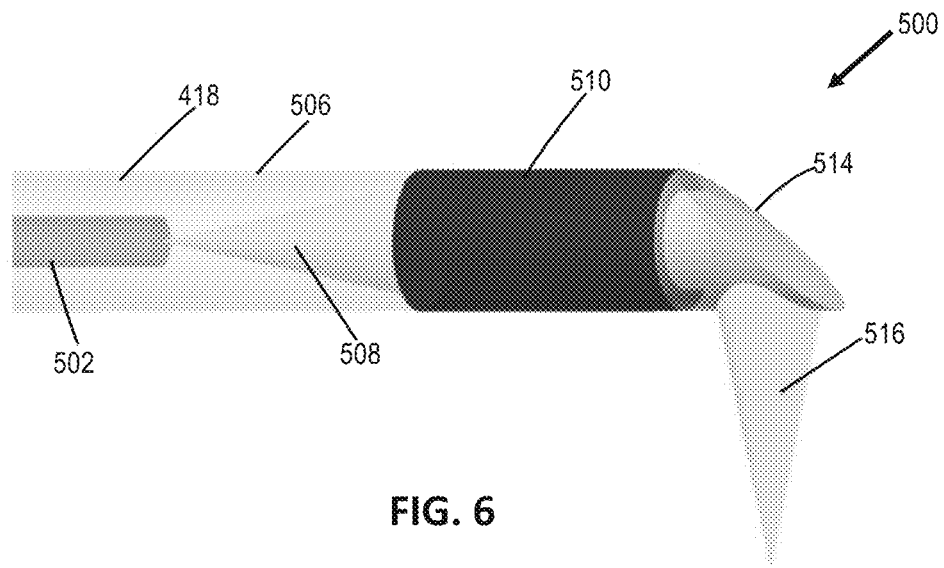
FIG. 6 shows an example embodiment of the fiber.
Figure 7:
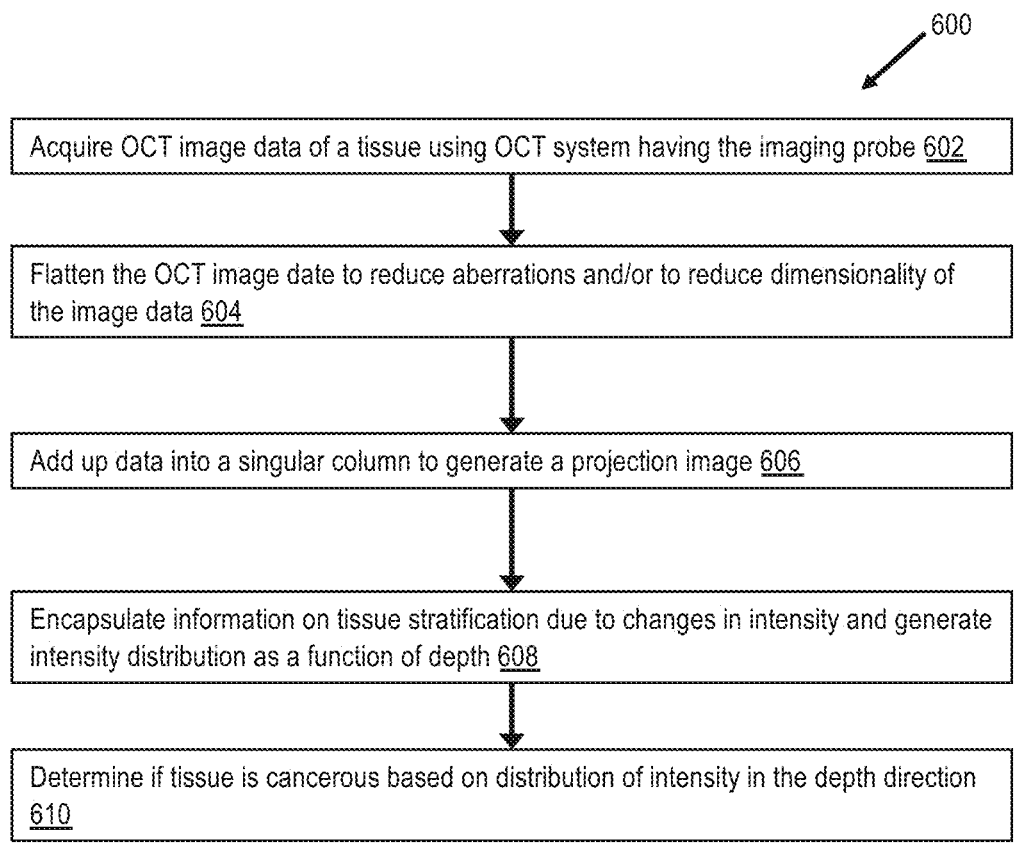
FIG. 7 shows a flow chart of an example method for processing OCT images obtained using the OCT imaging system to screen for cancer in tissues.

An example design (500) of the fiber (418) is shown in FIG. 6. The fiber (418) may include a fiber core (502). The fiber (418) may be additionally coupled to a coreless fiber or coreless portion (506). The coreless fiber (506) may include a focusing portion/fiber (510) and an angle cleaved portion (514) that focus and direct the light beam into the tissue (as indicated by cone 516). The fiber cored portion of the probe may include a core of a single fiber for propagating a single mode of light. The segment of coreless fiber (506) and the length of the GRIN focusing fiber (510) may be configured to tune the working distance and lateral resolution of the probe. The angle cleaved portion (514) of the probe may further include a gold coated surface to improve the internal reflection of the propagating beam out of the probe. In one non-limiting example, the coreless fiber optic (506), focusing fiber (510), and angle cleaved (514) distal portion of the probe may be realized as a fused fiber optic ball lens that allows for proper beam divergence as well as focusing. As such, the angle of cut of the angled portion (514) may be selected based on a desired viewing angle.

Figure 10:
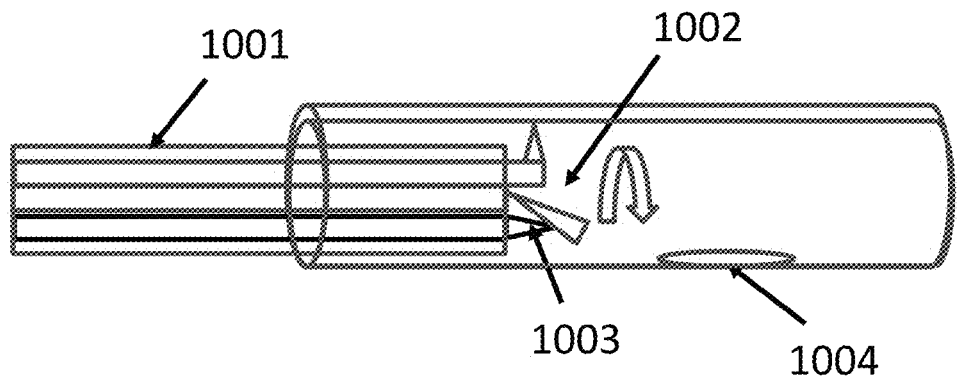
FIG. 10 shows an example of the device of the present invention comprising a fine needle aspiration biopsy needle.

In some embodiments, shown in FIG. 10, the OCT fiber (1002), may be placed inside a multi-lumen guide catheter (1001), alongside a fine-needle aspiration biopsy needle (1003). In this manner a suspicious tissue sample (1004) may be acquired immediately upon imaging and classification.

Figure 11:
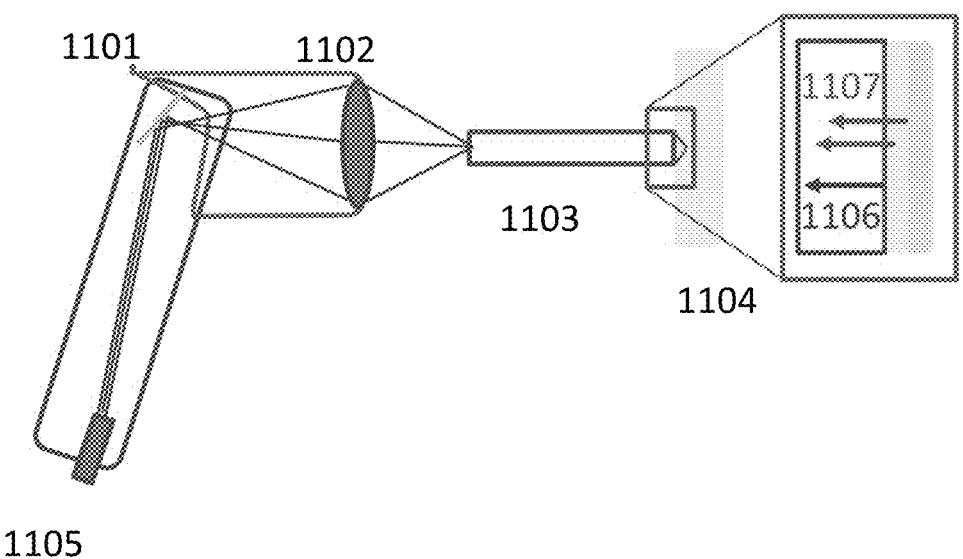
FIG. 11 shows an exemplary architecture for a common-path probe tip for optical coherence tomography.

In some embodiments, shown in FIG. 11, the imaging device may comprise a fiber optic collimator (1105), MEMS 2D mirror (1101) disposed to reflect the light into an objective lens, the objective lens (1102), and a 1-pitch GRIN rod (1103), used to project light into the sample (1104). This single path device allows both the reference light (1106) and light reflected by the sample (1107) to be received through the device, simplifying interferometry.

Figure 12:
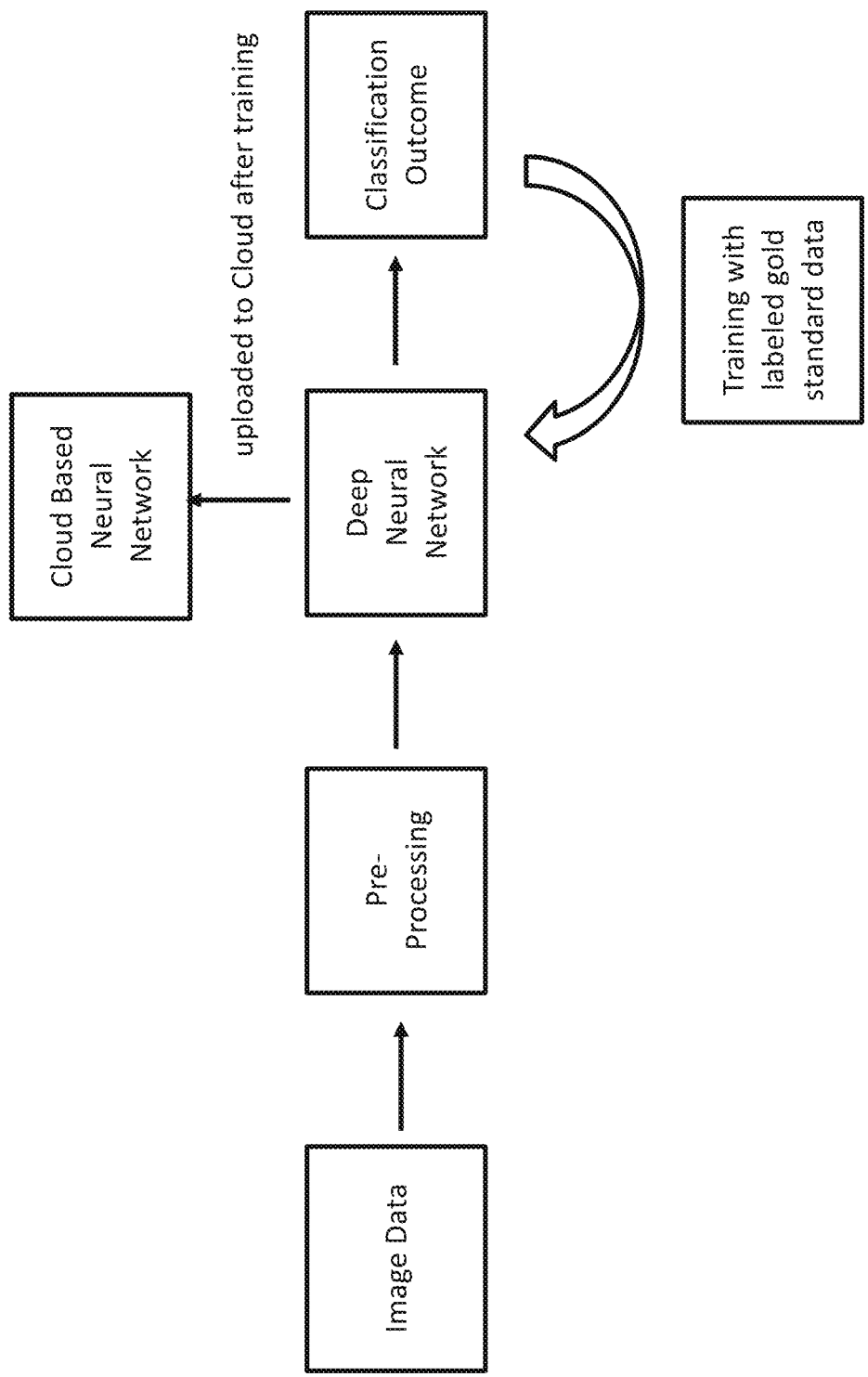
FIG. 12 shows an example process flow for training the device with freshly acquired data.
Figure 13:
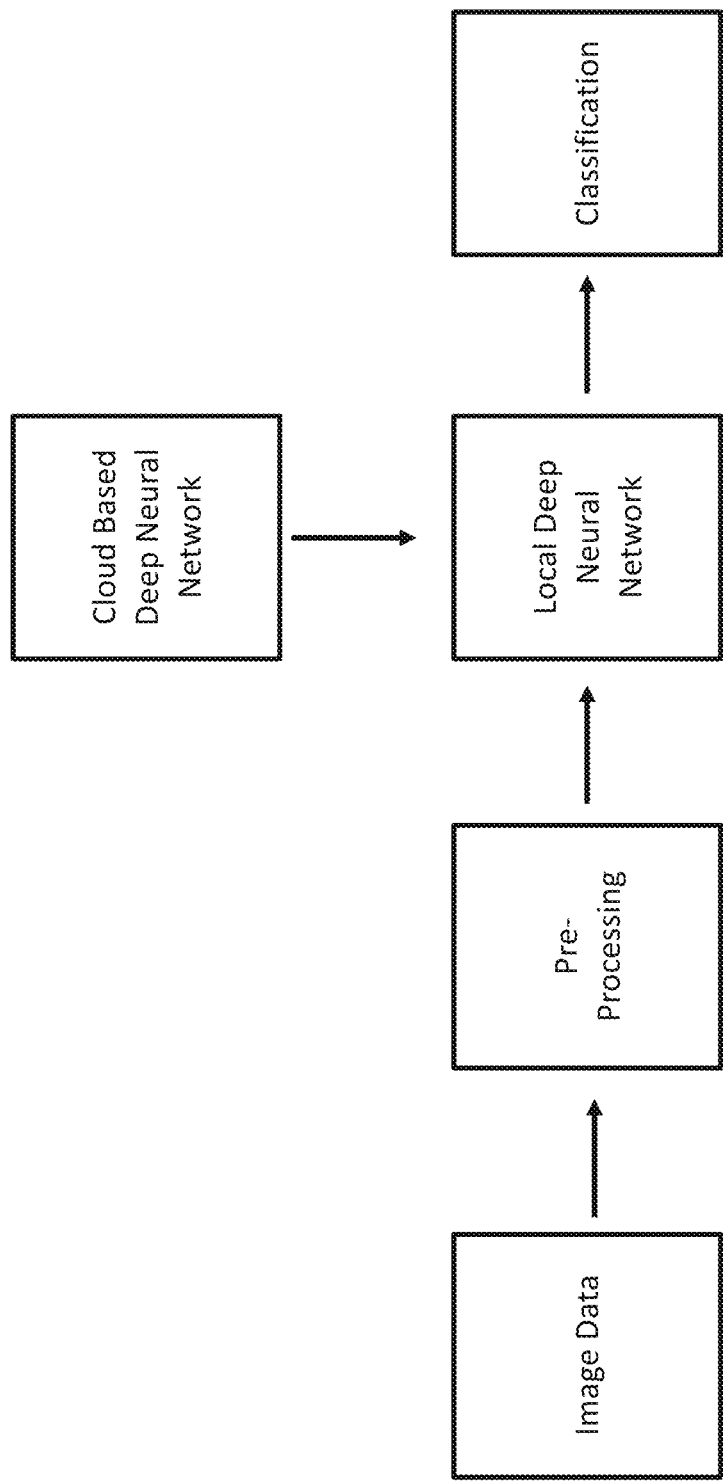
FIG. 13 shows and example process flow for using a deep learning network to perform classification on a sample.
Figure 14:
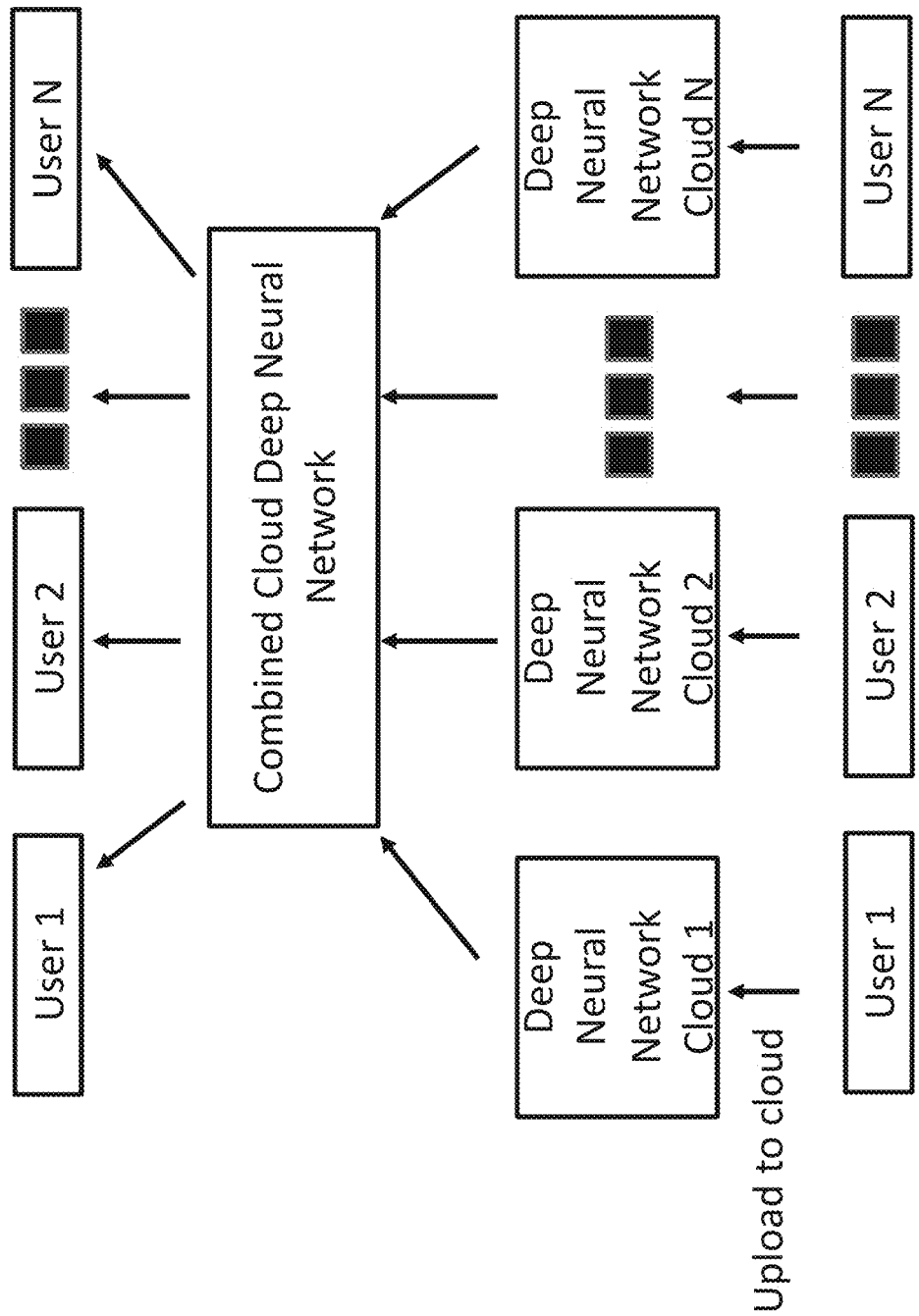
FIG. 14 shows a conceptual cloud-based computing architecture for uploading newly acquired tissue sample data, updating a shared deep learning network, and sharing the acquired updated parameters of the deep learning network with other devices.

In some embodiments, shown in FIG. 12, the supervised learning algorithm (940) may be a deep neural network (944). The deep neural network may be implemented on a cloud based platform. The screening device may be retrained using locally produced results for biopsied tissue samples and the updated network parameters uploaded to the cloud. In some embodiments, shown in FIG. 13, the screening device downloads updated parameters produced by other users. In some embodiments, shown in FIG. 14, the cloud implemented deep neural network is divided into set of sub-clouds which can be separately retrained and then combined.

Using the imaging probes described herein, OCT images of the tissue may be obtained. The OCT images may be further analyzed using an example method of FIG. 7. Instructions for carrying out method 600 may be executed by a processor (such as processor 220 of the optical system (102)) based on instructions stored on a memory of the processor and in conjunction with signals received from the optical and mechanical components of the imaging probe, described above with reference to FIGS. 2-6.

At 602, method 600 includes acquiring OCT image data of a tissue using an OCT imaging system having an imaging probe. In one non-limiting example, the OCT imaging system may be the optical system, (102) of FIG. 3, and the imaging probe may be the imaging probe (104) and/or imaging probe (406) of FIGS. 2 and 5, respectively.

In one example embodiment, the imaging system is a high speed swept-source based optical coherence tomography (OCT) system that is comprised of a vertical cavity surface emitting swept laser (VCSEL), fiber based Michelson interferometer, detection, and analog to digital conversion circuitry. During image acquisition, the imaging probe may be positioned within the tissue such that a circumferential view of the tissue may be obtained. In the case of the GRIN rod lens imaging probe, 2D data may be obtained by scanning the beam using the galvanic scanning mirrors. In the case of the fiber probe, to obtain 3D volumetric images, the probe may be linearly translated backward while being rotated.

OCT interference signals that are sampled with the high-speed analog to digital circuitry are then converted to gray scale images are then processed as described below. At 604, method 600 includes flattening the OCT image to a line to remove optical aberrations caused by the rod lens, for example. During flattening, a contour of a top surface of OCT image is identified by a surface tracing dynamic programming algorithm. The surface position and the data found underneath are shifted to a flat line to standardize the size of the image data set. Flattening the image results in reducing dimensionality of the data, thus causing an enhancement of the processing speed.

At 606, method 600 includes adding up the data into a singular column to generate an integrated projected image of the OCT signals. Then, at 608, the projected image is used to generate an intensity distribution as a function of depth (plot 706 of FIG. 7C). Finally, at 610, the intensity distribution is analyzed to determine if the tissue is cancerous or not.

In one example, the method initially analyzes the presences of a layered tissue structure through identifying peaks in the depth resolved intensity OCT signal. The lack of a layered structure has been shown in the literature to indicate invasive carcinoma as well as remodeling of the squamous epithelium caused by moderate to severe dysplasia. After determining the presence of a layered structure, the algorithm then analyzes the thickness of said layers to further classify the region of tissue into variable grades of dysplasia to guide the physician's biopsy or resection. Real time 2D cross sectional images of the lumen can be acquired at video rate (30-50 Fps) to further confirm the position of the biopsy or surgical tool and the gross anatomy.

In some examples, based on the depth resolved intensity distribution, a minimum of two peaks was observed in the non-malignant oral mucosal images, while only one peak was observed in images of cancerous tissues (FIGS. 8A-8F). From this analysis, the number of peaks was identified as primary diagnostic decision criterion. Using this the tissue is classified as malignant, dysplastic, and healthy. Experiment performed in the oral mucosa to classify oral tissue as healthy and dysplastic vs. malignant is shown in FIG. 8A-8C and FIG. 9A-9F.

Figure 8A:
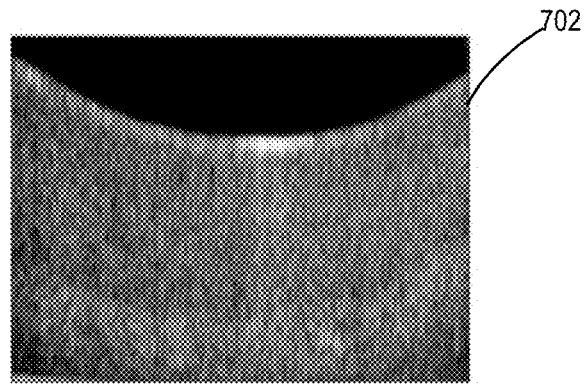
FIG. 8A shows an example OCT image acquired using the OCT imaging system.
Figure 8B:
FIG. 8B shows an example image generated by applying edge detection and flattening algorithm to the image of FIG. 8A.
Figure 8C:
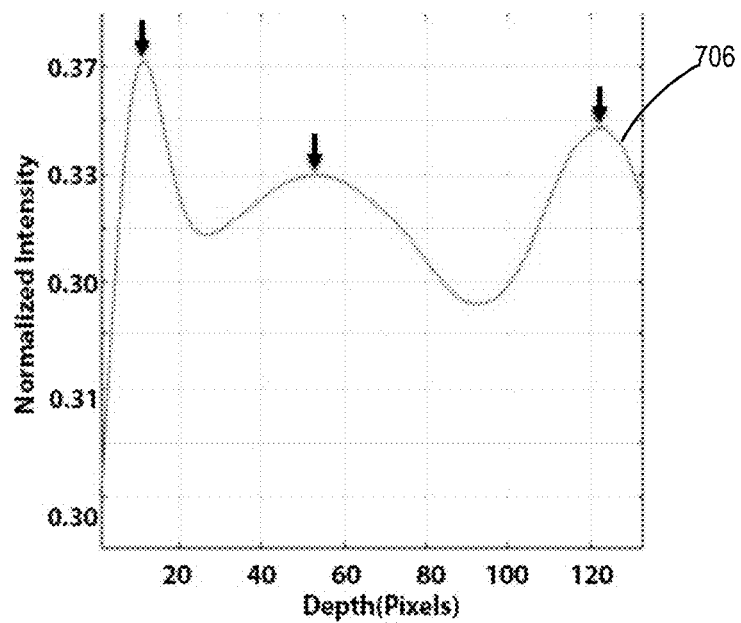
FIG. 8C shows an example depth intensity distribution.

Preprocessing of OCT images was necessary as imaging artifacts caused by spherical aberration in the probe design resulted in distorted OCT images 702 (FIG. 8A). To remove the distorted shape of the oral mucosa an edge detection and flattening algorithm was used. An example of a flattened image (704) is shown in FIG. 8B. OCT images were then classified as normal, dysplastic, and malignant through a two-step decision tree. Initially, OCT images were categorized into two categories: non-malignant (normal and dysplastic) vs malignant through a comparison of optical tissue stratification. Subsequently, the "non-malignant" group was broken down into characterization as either "healthy" or "dysplastic" by observing changes in the linearity of the basement membrane at the epithelium-lamina propria junction.

From a superficial observation, the presence of clear and organized epithelial stratification and boundaries in the OCT images can readily give the viewer a sense of tissue classification with regard to "non-malignant" vs "malignant". In images of non-malignant tissues, these were optically delineated for the epithelium and underlying lamina propria (images 802, 804, and 806 of FIG. 9A-B). However, in malignant lesions of the oral mucosa, tissue stratification (FIG. 9C) and basement membrane delineation were consistently absent. Based on these observations an algorithm was developed to analyze the depth resolved intensity distribution to distinguish images of non-malignant tissues from those of malignant sites.

Figure 9A:
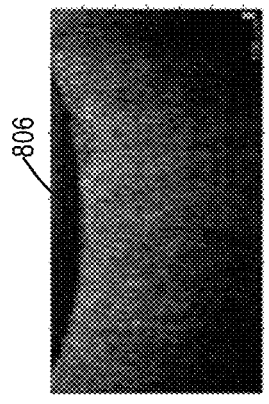
FIGS. 9A-9F show example OCT images of normal, dysplastic, and malignant oral mucosa (FIG. 9A-9C), respectively, with corresponding depth resolved intensity distribution (FIG. 9D-9F).
Figure 9B:
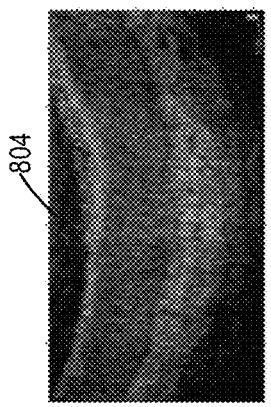
Figure 9C:
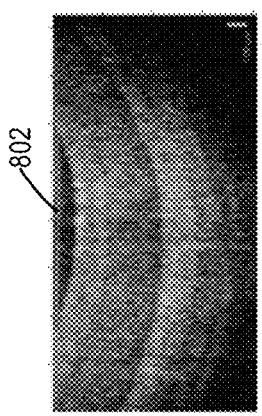
Figure 9D:
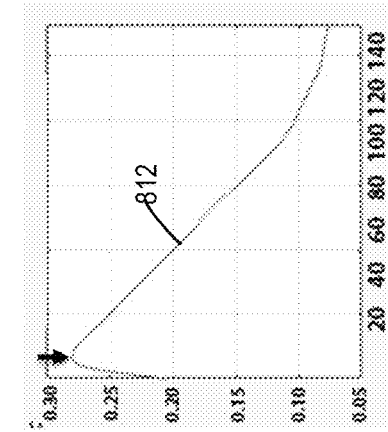
Figure 9E:
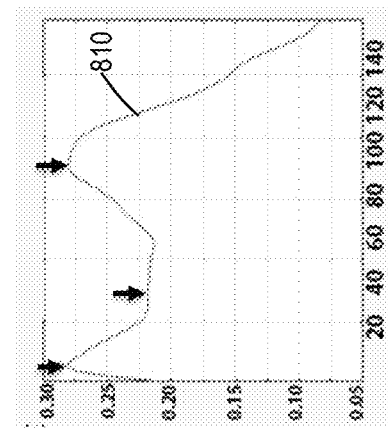
Figure 9F:
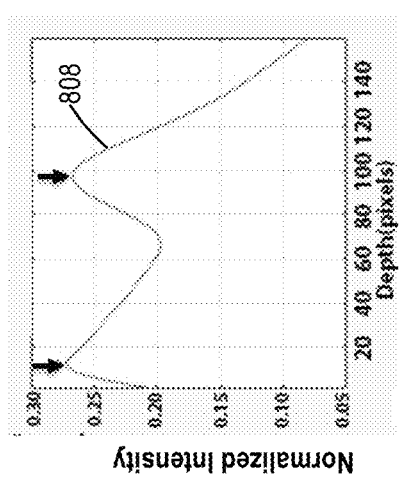

Firstly, a region of interest (ROI) was selected from the original OCT image. An edge detection algorithm previously developed was applied on the ROI to obtain the edge of the first layer. The tissue under consideration was then flattened to a given height with respect to the edge previously found. After flattening, averaging was conducted across the lateral direction of the image. The intensity of every 5 horizontal B-lines was averaged to smooth out the depth resolved intensity distribution. Finally, the intensity depth distribution was averaged using a 20-point sliding window to remove the small peaks in intensity along the depth direction (FIG. 9C)

Based on the depth resolved intensity distribution, a minimum of two peaks was observed in the non-malignant oral mucosal images, while only one peak was observed in images of cancerous tissues (plots 808, 810, and 812 of FIGS. 8D-F). From this analysis, the number of peaks was identified as primary diagnostic decision criterion. Using this rudimentary algorithm, 10 images each of malignant, dysplastic, and healthy oral mucosa were analyzed. Thus, the proposed OCT-based approach can improve the diagnostic accuracy when an oral oncologist evaluates an oral lesion.

Example 1

The following is a non-limiting example of the present invention. It is to be understood that said example is not intended to limit the present invention in any way. Equivalents or substitutes are within the scope of the present invention.

Introduction:

Incomplete surgical resection of head and neck cancer lesions is the most common cause of local cancer recurrence. Currently, surgeons rely on their experience of direct visualization, palpation, and pre-operative imaging to determine the extent of tissue resection. Intraoperative frozen section microscopy is used to assess presence of cancer at the surgical margin. It has been demonstrated that optical coherence tomography (OCT), a minimally invasive, non-ionizing near infrared mesoscopic imaging modality can resolve subsurface differences between normal and abnormal oral mucosa. However, previous work has utilized 2-D OCT imaging which is limited to the evaluation of a small regions of interest generated frame by frame. OCT technology now can perform rapid volumetric imaging, but the capacity and expertise to analyze this massive amount of image data is lacking. This example demonstrates a proof-of-concept that re-trained convolutional neural network is capable of analyzing 3-D OCT images of oral mucosa in order to differentiate normal and abnormal tissues specifically pertaining to head and neck squamous cell carcinoma (HNSCC).

Methods:

Patients undergoing surgical resection of oral squamous cell carcinoma (SCC) were identified and enrolled in this cross-sectional study. Following resection, the specimen was scanned using a vertical cavity surface emitting laser (VCSEL) 1310 nm center wavelength OCT microscope system. Acquired 3-D volumetric OCT data was labeled by co-registered histopathology and split into a training and test set. Supervised training of a pre-existing convolutional neural network (CNN), AlexNet was conducted through transfer learning. The CNN classification accuracy was then assessed with the test set OCT margin data Results:

Seven resected specimens were imaged at the tissue margins. OCT images were correlated with histopathology. Calculated sensitivity and specificity were 100% and 70% respectively for normal and dysplastic or malignant mucosal differentiation associated with negative and positive margins.

Conclusion:

Supervised transfer learning of pre-existing convolutional neural networks can differentiate healthy and dysplastic or malignant tissue changes of the oral cavity and oropharyngeal epithelium. This method has the potential to serve as a real-time analytic tool in the assessment of surgical margins. Further in vivo studies are required to assess the use of this algorithm of assessing tissue margins in the resected bed and deep tissue sites.

Introduction:

Successful surgical treatment of head and neck squamous cell carcinoma (HNSCC) relies on achieving resection margins clear of tumor. Depending upon the location within the head and neck, surgeons will resect a few millimeters in the larynx to 2 cm around tongue lesions to remove microscopic residual tumor in the tissue bed. Computed tomography (CT) imaging can aid in pre-operative planning of tumor resection but is limited in resolution and tissue contrast; it is largely used to guide macroscopic resection. Intraoperatively, surgeons visualize and palpate tissue to estimate the resection margin. Most commonly, frozen section histology the resection margin (read by a pathologist) provides rapid and reasonably accurate determination of the presence of cancer cells. However, frozen section is limited in terms of the total volume of tissue that can be evaluated, as analysis takes considerable time, and only a sample of the true margin can be evaluated. Despite clear surgical margins using frozen section guidance margins, 25% surgically treated HNSCC develop cancer recurrence. This is could be partially accounted for by the limitations and sampling error in the frozen biopsy sections along with artifact that occurs during sample preparation particularly in specimens with complex topology such as at the base of tongue and larynx.

Non-invasive imaging modalities such as: optical coherence tomography (OCT), auto-fluorescence imaging, confocal microscopy, narrow band imaging (NBI), and Raman spectroscopy may aid in the non-invasive assessment of tumor margins. These technologies are rapid and also could potentially be used in situ as well as in specimens that have been freshly resected. Of the aforementioned imaging modalities, OCT is unique in that it provides near histopathological resolution cross-sectional images of tissues in real time, a desirable aspect of a tool developed for intraoperative use. OCT uses differences in tissue optical properties (chiefly optical scattering) to generate tissue contrast. Contrast does not: 1) depend upon biochemical absorbers such as in fluorescence imaging; 2) require the use of dyes, stains; and 3) does not require special modification of operating room ambient lighting such as in many fluorescent techniques. OCT has been shown to differentiate normal and abnormal oral mucosa. However, direct subjective interpretation of OCT images by human observers requires extensive cumbersome training. Since contemporary OCT systems may acquire up to 40 images/second, this massive amount of data poses a challenge for clinical implementation.

To address this challenge, many research groups have developed automated or semi-automated image processing techniques that provide quantifiable metrics to separate and categorize OCT images into healthy, dysplastic and malignant classifications. Prestin et. al demonstrated an offline digital morphometry image processing method that measured epithelial thickness in OCT images to grade the extent of dysplasia based upon normative values. Lee et. al demonstrated the ability to differentiate normal and pre-malignant dysplastic oral mucosa through the standard deviation of the scattered intensity signal at the epithelial lamina propria junction. Tsai et. al present an OCT intensity image processing method sensitive to the cellular homogeneity or heterogeneity of the epithelium and basement that was found to represent differences between normal and malignant mucosa. Lastly, Pande et al. introduce a method to quantify the depth resolved intensity structure of the tissue that encapsulates pre-malignant changes to normal oral mucosa in a hamster cheek pouch model. Previous OCT oral cancer image processing literature has shown that OCT data indeed has the potential to identify and distinguish tissue changes from dysplasia to carcinoma in situ to invasive cancer in the oral mucosa in images generated using 2-D scanning geometry. However, there are few studies exploring the use of 3-D OCT to evaluate these changes in part because of the sheer volume of data generated with such technology. Additionally, it is unclear whether a combination of the previously mentioned image classification approaches could provide a more robust and accurate bias free rubric. With the advent of highly-parallel graphical processing power and deep learning techniques, "intelligent" system offer potential as a means to classify data when certainty of diagnosis may be sublime, and this hold promise at the very least as a screening measure or biopsy/margin resection guidance measure with OCT.

Deep learning, a subfield of machine learning leverages the structure of neural network to learn how to classify data. Deep learning method have found widespread use across fields such as bioinformatics, healthcare and image recognition for skin cancer diagnosis. A neural network is comprised of a series of neural layers that are further comprised of neurons. In the circumstance of a convolutional neural network each neuron. A neuron holds a value called an activation that dictates Supervised learning, a deep learning methodology, trains a layered network to classify input data based on its labels. As labeled data is progressively fed into the network the network improves its classification ability through adjusting weights located at each neuron to minimize the error of the classifications. Convolutional neural networks (CNN), a type of network trained commonly through a supervised learning method is capable of differentiating images based upon their abstraction by convolution filters. A convolutional filter is used to condense data in each kernel or sub-matrix of an image through element matrix multiplication and summation. Through such processes specific convolutional filters can be designed to extract classifying characteristics of 2-D image data. In order to overcome the often-large data sets needed to sufficiently train a CNN from scratch, it has been found that a pre-existing CNN can be re-trained using transfer learning. In this study we leverage this aspect of re-training a preexisting CNN on a smaller data set to assess the feasibility of utilizing such a CNN to classify oral cancer margins in 3-D OCT image volumes.

Swept Source OCT Imaging System Probe

Figure 15:
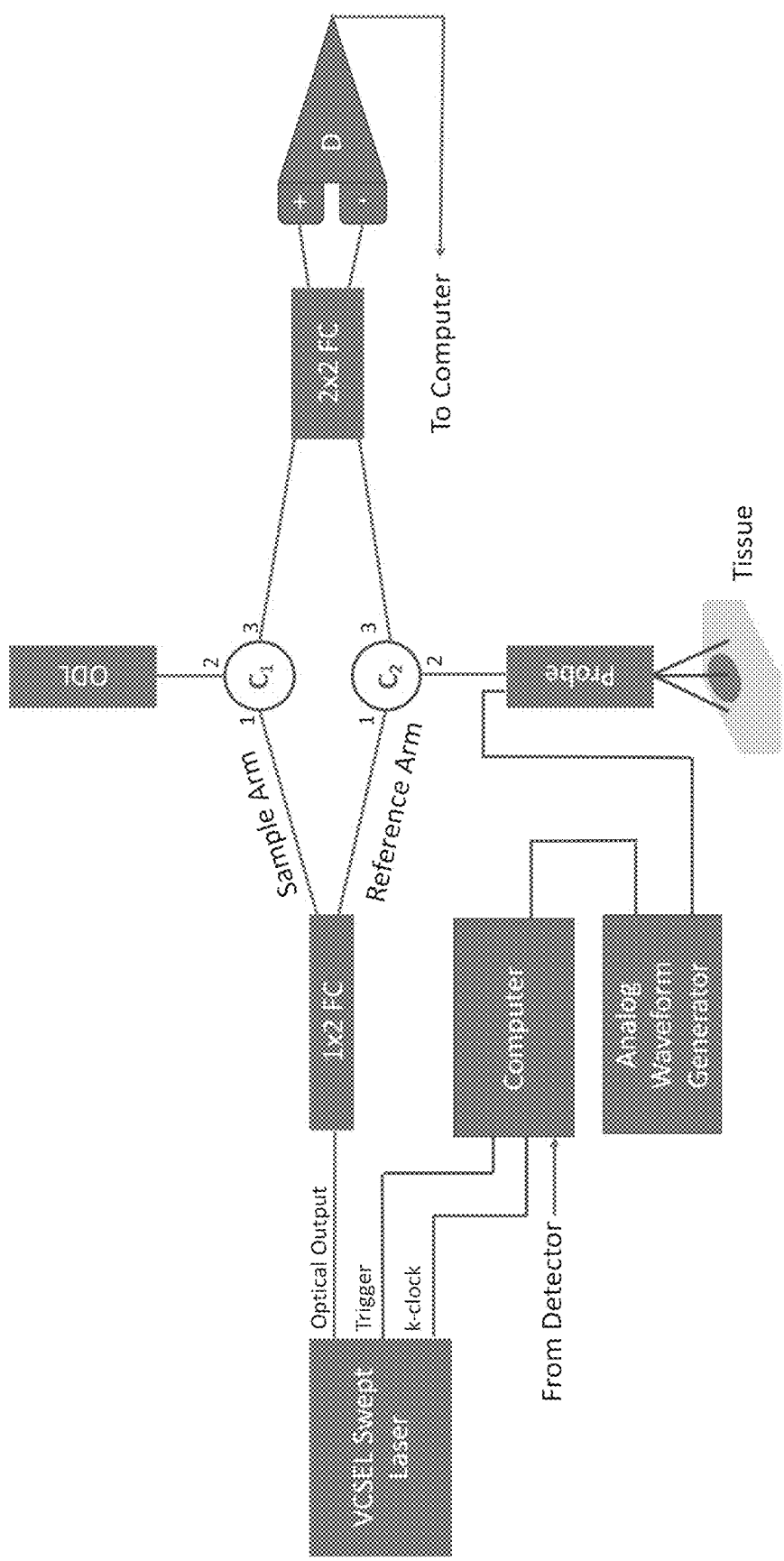
FIG. 15 shows an example imaging device architecture for performing OCT image acquisition using Michelson-based interferometry. ODL: Optical delay line used to match the optical path length of the sample arm, FC: In line fiber optic coupler used to split and combine the laser light used in the interferometer, D: Balanced photodiode used to detect the interference OCT signal, C1,2: Fiber optic in-line circulator used to direct the representative sample and reference beams.

A VCSEL OCT system and microscope scanning probe was utilized to classify tissue as healthy or cancerous. A fiber based commercial swept source OCT system and microscope scanning probe were utilized for this study. A diagram of the system can be seen in FIG. 15.

Laser output light from the 200 kHz SS VCSEL laser (ThorLabs, New Jersey) $\lambda=1310$ nm $\Delta=100$ nm, was coupled into a fiber optic Michelson interferometer via a 1×2 10:90 fiber coupler (FC) split between the reference arm (10%) and sample arm (90%). The output of the fiber coupler is fed into an in-line fiber optic circulator to collect the back reflected light from both the sample and reference arm. The sample arm is comprised of a typical 3-D scanning OCT imaging probe seen in FIG. 15. Input light into the probe is collimated and directed onto a pair of X-Y gold coated galvanometer mirrors. The beam is then scanned across a microscope scan (ThorLabs Scan lens) lens that focuses the light into the tissue. The reference arm of the OCT system is comprised of a tunable reflection style air delay. The reference and sample arm signals are then recombined by a 2×2 50:50 FC and detected across a balanced photodiode detector. OCT interferograms were digitized with respect to an output frame trigger and a non-linear k-clock signal from the VCSEL laser. Raw data interferograms were processed at 200 fps using CUDA graphical processing unit (GPU) based computation.

Cancer Resection and 3-D OCT Imaging

Seven patients with HNSCC treated at the University California Irvine Medical Center (UCIMC) were enrolled and consented to image their resected main cancer specimen. Patient demographics used for the purpose of this study are summarized in Table I. Patient consent and Imaging protocol abides by UCI IRB2003-3025.

TABLE 1

| Patient Demographics | |
|---|---|
| Number of Patients | 10 |
| Male | 7 |
| Female | 3 |
| Types of Cancer | |
| Squamous Cell Carcinoma | 6 |
| Positive Margins | 2 |
| Negative Margins | 4 |

TABLE 1-continued

| Patient Demographics | |
|---|---|
| Number of Patients | 10 |
| Cancer Organ Origin | |
| Tonsil | 3 |
| Soft Palate | 2 |
| Tongue | 3 |
| Lower Lip | 1 |
| Floor of Mouth | 2 |
| Buccal Mucosa | 1 |

Following resection, cancer specimens were transported to the pathology department where multiple margins and visible transition zones between normal epithelium and frank invasive cancer were imaged with 3-D OCT as can be seen in FIG. 17A-F.

Specimen orientation was performed by the attending surgeon in the presence of both research staff and the attending pathologist. Several 7 mm×7 mm 3-D OCT image volumes consisting of 1,000 B-scans were acquired at each site of clinical interest (as determined by the attending surgeon). Every selected location was also imaged with conventional digital video accompanied by an audio recording to aid with later analysis. Audio records provide clinical detail on the orientation of the specimen, the geometric location, and clinical relevance. This is important in the head and neck where the topology of the tumor margin is exceptional complex. Digital video acquired from an oblique angle displays a co-registered red aiming beam that coincides with physical location of the region imaged using OCT. Acquisition time for each 3D volume was 7 seconds. It should be noted that OCT imaging did not slow the process frozen section analysis of the tissue specimens. Such frozen biopsies were not scanned. After imaging, the main specimen was sectioned by a technician and placed into 10% neutral buffered formalin to prepare for imbedding, sectioning, hematoxylin and eosin (H&E) staining, and later off line analysis by a pathologist.

OCT Image Pre-Processing

OCT raw interferogram data were converted into log-based power spectrum data and normalized. The gray scale OCT data was false colored yellow to blue corresponding to high and low OCT signal intensities to visualize localized intensity gradients more readily. OCT images were then saved as .jpg images that would then be utilized in the re-training of a pre-existing convolutional neural network (ImageNet).

Oral Cancer Net Transfer Learning

Figure 16:
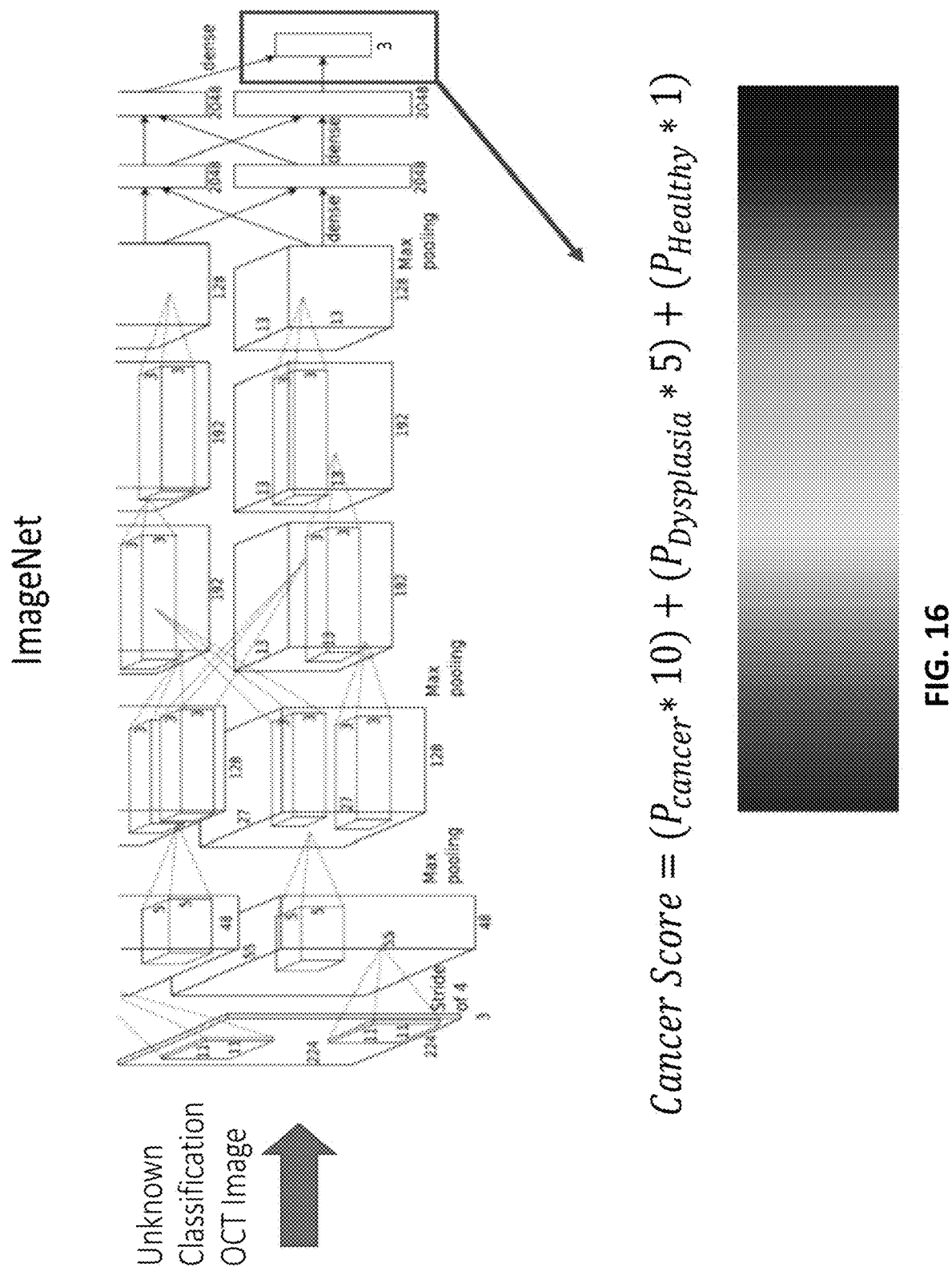
FIG. 16 shows an example of a deep learning network outputting a classification score for an input image.

ImageNet, later renamed, AlexNet created by Alex Krizhevsky et al is a CNN that has been trained on 1.2 million high-resolution images of 1000 different classes (FIG. 16). AlexNet was re-trained by a supervised learning technique using the MATLAB (Natick, Mass.) machine learning toolbox called transfer learning that builds upon the pre-existing CNN.

Figure 18:
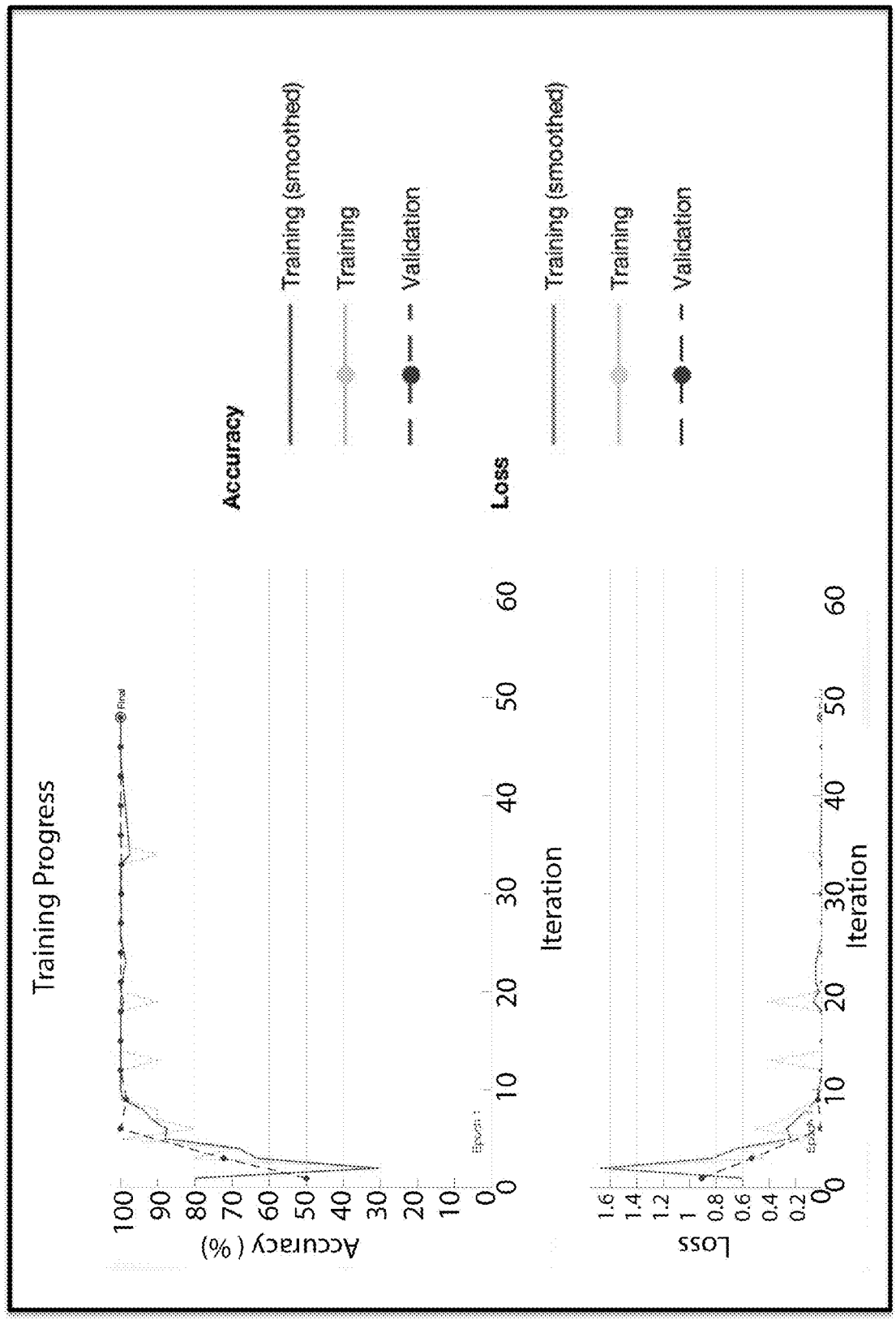
FIG. 18 shows graphical depictions of accuracy and loss training record for the supervised transfer learning for AlexNet with the OCT head and neck cancer images obtained in Example 1.
Figure 19A:
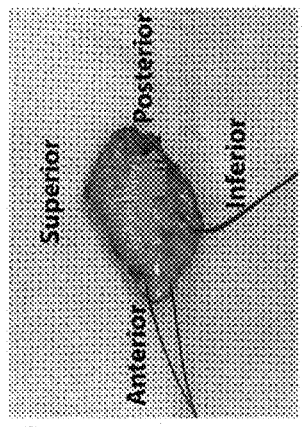
FIGS. 19A-I show tissue scanning data obtained in Example 1.
Figure 19B:
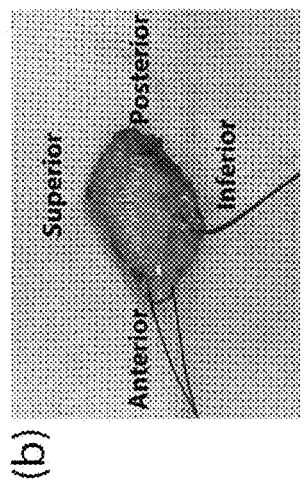
Figure 19C:
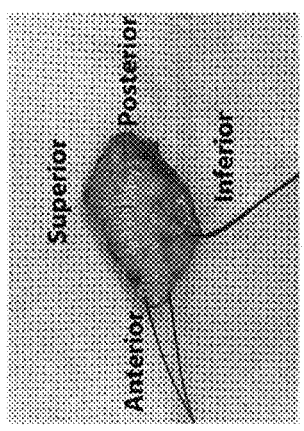
Figure 19D:
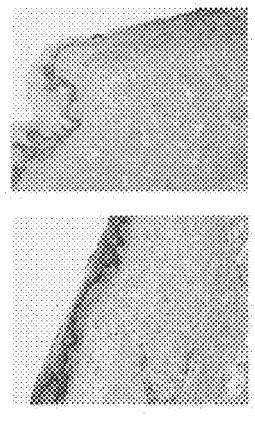
Figure 19E:
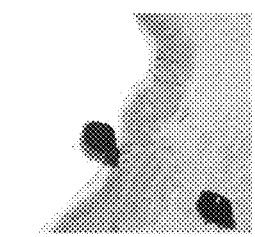
Figure 19F:
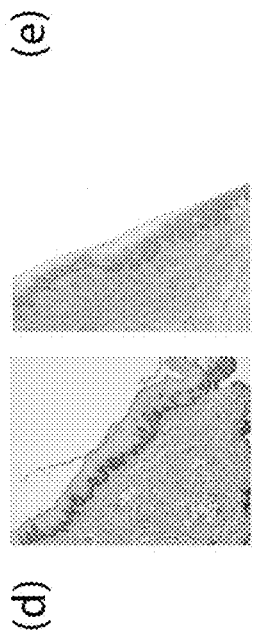
Figure 19G:
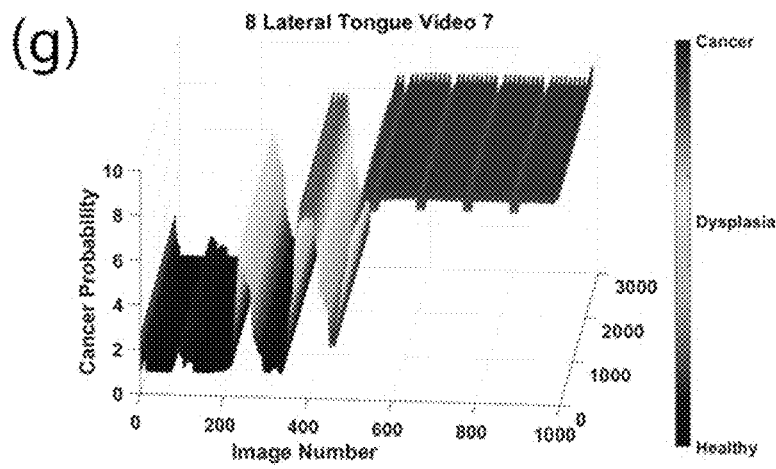
Figure 19H:
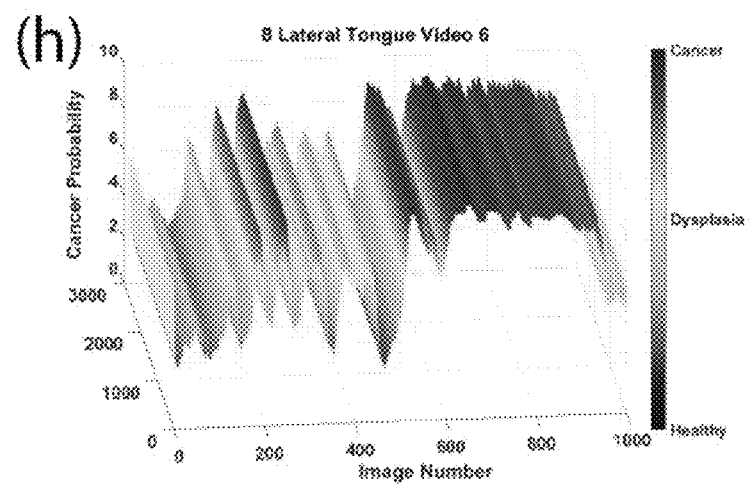
Figure 19I:
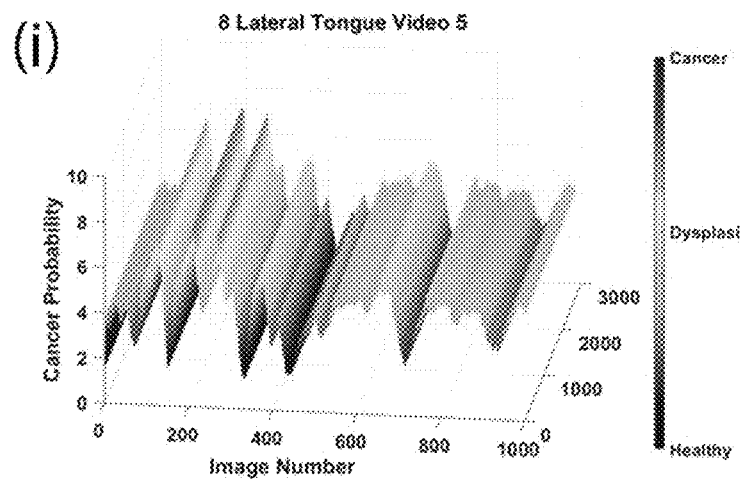

The CNN was loaded into MATLAB as an object comprising a series of layers. The last layer of the pre-existing CNN used for classification was removed and replaced with the custom classifiers of the oral mucosa namely normal, dysplastic, and malignant. A total of 33 image volumes each comprising of 1,000 B-Scan OCT images were acquired across 7 head and neck cancer patients. Twenty-two of the image volumes were co-registered with histopathological labels and thus were usable for training and validation of the CNN. Of the 22 image volumes 30% or approximately 6 volumes were used for training and the remaining 70% was used for validation. The 6 training data set volumes included 2 volumes of healthy, dysplastic and malignant oral cancer images. Both the training and validation OCT B-scan images were randomly shuffled and loaded into data structures that could then be used to train the CNN in MATLAB. Using a single graphics processing unit (Nvida GTX 1080), the CNN was re-trained for 120 iterations. Real-time training accuracy and validation were plotted in MATLAB that can (see FIG. 18). The CNN is seen to converge to greater than 95% accuracy within 40 training iterations taking approximately 6' 35". The re-trained neural network was then used to classify the 3-D OCT validation set excluded from the training set.

Classification Criterion

The CNN classification of a given OCT B-scan is determined by the probability that the input image belongs to 1 of the 3 classification categories. This probability distribution of cancerous, dysplastic and normal is then mapped to an RGB spectrum to ease the interpretation of the 3-D volumetric OCT data FIG. 16. The probability that the image under question was scaled in a range from 1 to 10. The probability of cancerous classification was multiplied by 10, dysplastic probability was by 5 and normal by 1.

For the purposes of this study histopathologic labels for each individual B-scan was not practical in each volume due to the cumbersome and impractical task of serially sectioning the main specimen at 15 mm thickness for a length of 7 mm. Instead, a single histopathologic section provided from an area scanned was used for sensitivity and specificity calculation of the CNN classifier. Through interpretation of the pathology report in conversation with a pathologist, corresponding histopathology was determined for a given OCT 3-D volume. Volumetric classification of an entire OCT image volume was determined by the distribution of images classified as a cancerous, dysplastic, or normal FIGS. 19A-I. A percentage normal or abnormal was calculated by Equation 1. Based upon the higher percentage a given OCT volume was characterized as normal or abnormal.

Equation 1

$$P_{normal} = \frac{(\text{\# Images Normal} + \text{\# Images Dysplastic})}{(\text{\# Total Images})} \quad (1)$$

$$P_{abnormal} = \frac{(\text{\# Images Cancerous} + \text{\# Images Dysplastic})}{(\text{\# Total Images})}$$

Results

Figure 20:
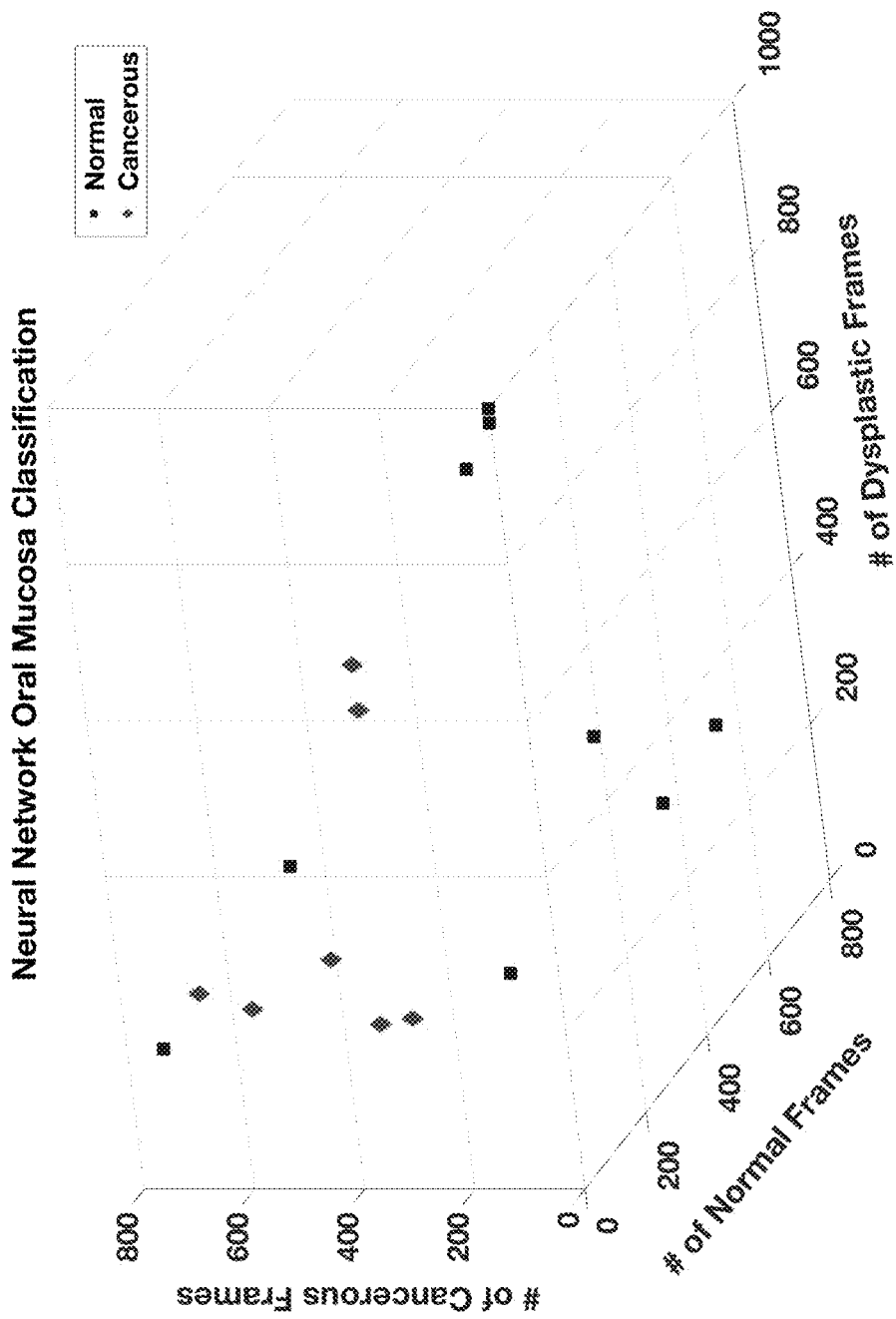
FIG. 20 shows a graphical representation of the results of the neural network classification for all image volumes acquired in Example 1.

Three-dimensional OCT image volumes from 7 head and neck cancer patients were included in the sensitivity and specificity assessment of the re-trained CNN. The respective number of abnormal and normal images for each OCT image volume can be seen in FIG. 20. The calculated sensitivity, specificity, and accuracy of the CNN to correctly classify an unknown OCT 3-D volume image as positive for cancer was found to be 100%, 70%, and 82% respectively. Abnormal OCT 3-D CNN classification volumes had an average of 792 abnormal images with a standard deviation of ±165 and an average of 465 images with a standard deviation of ±151. Normal classification OCT 3-D CNN classification was found to have an average of 660 normal images with a standard deviation of ±235 and an average of 551 abnormal images with a standard deviation of ±233.

Discussion

This example has shown that a pre-existing convolutional neural network, AlexNet, after transfer learning is capable of potentially classifying 3-D mucosal head and neck cancer OCT image volumes into normal, dysplastic, and cancerous categories. This study is believed to be the first investigation of a CNN to classify normal and abnormal head and neck mucosal tissue, showing potential as a means to rapidly interpret intraoperative HNSCC tissue margins. The organs within the head, neck, and upper airway all share in common a complex surface geometry, unlike planar structures such as the skin. Hence, determination of clear margins, or margins with a high probability of being clear would be valuable to improve full resection of tumor. At present, such margin determination relies entirely upon clinical judgment combined with frozen section analysis. Augmenting this process could improve the process of definitive margin identification and simplify surgery.

Six thousand images from four patients were utilized as a training data set. Although a limited number of training images were used, a re-trained CNN can reasonably separate normal and abnormal oral mucosa. With a sensitivity and specificity of 100% and 70%, respectively the CNN tends to over diagnose classifying normal tissue as abnormal. This is a positive attribute to a reasonable extent in the setting of clearing resection margins, ensuring that no cancer is included in the margin. Previous work has showed the efficacy of using CNN to diagnose various ophthalmic disease pathologies suggesting that CNN could be used differentiate OCT images of varied disease pathologies provided a substantially large data set. Comparing the accuracy of the CNN with previously investigated parametric classifying algorithms for margination we see comparable sensitivity and specificity.

There exists image processing techniques that have been used to classify oral cancer lesions using small sets of individual 2-D OCT B-scans, but to date no automated approach has been adapted to handle the massive data generated with 3-D OCT data in terms of cancer diagnostics. Three-dimensional anatomically co-registered OCT imaging of head and neck cancerous lesions is imperative to insuring cancer free margins. As can be seen in FIGS. 19A-I, traditional approach of 2-D OCT imaging may have missed a portion of potentially cancerous tissue at the anterior edge of the sample. Interestingly this patient was found to have clean frozen biopsies intra operatively and involved margins in permanent section requiring further surgical intervention. From this example we are able to see the potential power of OCT to guide further frozen sectioning or to serve as a diagnostic adjunct capable of rapidly assessing the surgical field for remaining cancer or clean margins.

Although the retrained CNN performed well with an accuracy of 82% there are several limitations to this study. The first limitation being the provided histopathology for label verification of corresponding OCT images. Finer histopathological sections across a block specimen are typically not provided due to the resulting time required to complete such a task. This is a result of traditional permanent section histopathology of HNSCC main specimens that typically are submitted for block sections closest to margin of the grossly identified tumor mass. This tedious time-consuming workflow including embedding, slicing, transferring the thin microns thick slices to a slide and staining. This multi-step process sheds light onto possible limitations of current pathology that could benefit from future improvements in automation. Secondly, inflammation, hyperkeratosis, non-cancerous cellular changes induced by human papillomavirus (HPV), and high-grade dysplasia could be mistaken for carcinoma in-situ on OCT images seen as hyper reflective scattered signals. This can lead to a high degree of false positives for the neural network classification, ultimately affecting the accuracy of classification. This limitation can be overcome by training the network with sufficiently large datasets of variable tissue type confirmed by detailed histopathological sectioning. Lastly, due to the limited penetration depth of OCT at ~1-2 mm, intact, well stratified tissues with involvement deep within the lamina propria may be mis-classified by the CNN. This shortcoming could be improved by utilizing longer wavelengths such as 1.7 um lasers to penetrate deeper into the lamina propria to catch such abnormalities.

Future studies and hardware improvements could greatly improve the efficacy of using OCT and a CNN to differentiate normal and abnormal head and neck mucosal tissue without the need of an expert reader. Such work would include scanning the entirety of the mucosal surface of the sample in a mosaic pattern using a 2-D translational stage. Acquiring a comprehensive end-to-end data set representation of the specimen would allow for precise co-registration between the histopathological sections and the scanned area. In addition, providing a rich data set to further train the CNN on subtle variations between normal, dysplastic, and cancerous disease states. Additionally, improvements could be made to the CNN architecture to simplify the complexity of the number and variety of layer types. This could significantly improve training time and reduce the chance of overfitting of the data.

CONCLUSION

It has been shown for the first time that non-invasive OCT 3-D volumetric imaging of head and neck mucosal margins can be reasonably classified into normal and abnormal tissue pathologies with a CNN without the need of an expert reader. Such a technologic paring could provide great utility as an adjunct to traditional intra operative surgical palpation and frozen section assessment of tissue involvement. Further OCT data collection co-registered with finely sectioned histology will need to be conducted to provide further classifying power of the trained CNN. This example shows that CNN can differentiate normal and abnormal head and neck cancerous pathologies.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A device (900) for in-situ or in-vivo tissue cancer screening, capable of classifying observed tissue in real time, the device (900) comprising:
   a. an imaging device (910) capable of scanning a tissue sample, the imaging device (910) configured to determine a periodic time interval (918) and generate imaging frames (912) of a tissue sample (913) within the periodic time interval (918), wherein the imaging frames comprise a scan across the tissue sample;
   b. means for observing the sample region being scanned at the time of each imaging frame;
   c. an output device; and
   d. a device processor (930), operationally connected to the imaging device (910) and the output device, wherein the device processor (930) is configured to execute computer-readable instructions comprising:
      i. receiving a plurality of imaging frames (912) from the imaging device (910);
      ii. identifying the location of the imaging frames (915) within a common reference frame;
      iii. pre-processing the image frames (912) to prepare them for classification;
      iv. using a pre-trained supervised learning algorithm (940) to classify the image frames (912) within a plurality of classifications, wherein the supervised learning algorithm takes as inputs the positions of the imaging frames within the camera image, and the imaging frames, and produces as an output a classification (946); and
      v. reporting the classification (946) of the image frame to a user using the output device (920);
   wherein within the periodic time interval determined by the imaging device (910), the device processor (930) is capable of generating the classification (946) after generating the imaging frames (912) by the imaging device (910).

2. A device (900) for in-situ or in-vivo tissue cancer screening, capable of classifying observed tissue in real time, the device (900) comprising:
   a. an imaging device (910) capable of scanning a tissue sample, the imaging device (910) configured to determine a periodic time interval (918) and generate imaging frames (912) of a tissue sample (913) within the periodic time interval (918), wherein the imaging frames comprise a scan across the tissue sample;
   b. a camera (911), disposed to observe the area of the sample being scanned by the imaging device, the camera (911) capable of generating a camera image of the sample (913), wherein the camera image comprises a reference frame;
   c. an output device; and
   d. a device processor (930), operationally connected to the imaging device (910) and the output device, wherein the device processor (930) is configured to execute computer-readable instructions comprising:
      i. receiving a plurality of imaging frames (912) from the imaging device (910);

ii. receiving a camera image (914) from the camera (911);
iii. identifying the position of the imaging frames (915) within the reference frame of the camera image (914);
iv. pre-processing the image frames (912) to prepare them for classification;
v. using a pre-trained supervised learning algorithm (940) to classify the image frames (912) within a plurality of classifications, wherein the supervised learning algorithm takes as inputs the positions of the imaging frames within the camera image, and the imaging frames, and produces as an output a classification (946); and
vi. reporting the classification (946) of the image frame to a user using the output device (920);
wherein within the periodic time interval determined by the imaging device (910), the device processor (930) is capable of generating the classification (946) after generating the imaging frames (912) by the imaging device (910).

3. The device of claim 2, wherein the classifications (946) comprise a healthy class and a malignant class, and wherein the supervised learning algorithm (940) has been trained on a training data set (942) comprising sample images (943) of tissue with known classifications (946).

4. The device of claim 2, wherein the supervised learning algorithm (940) is a convolutional neural network (944).

5. The device of claim 2, wherein the periodic time interval (918) of the imaging device (910) and the time the processor (930) takes to classify the image frame (912) at each time interval is one second or less.

6. The device of claim 2, wherein pre-processing the image frame (912) to prepare it for classification comprises:
   a. determining an edge (913) of the image (912);
   b. flattening the image (912) based on the edge (913);
   c. normalizing and scaling the intensity of the image;
   d. selecting a region of interest (ROI) (914) of the flattened image (912); and
   e. generating a depth resolved intensity distribution (916) of the ROI (914).

7. A system (901) for generating in-situ or in-vivo classifications of tissue-samples in real time, the system (901) comprising:
   a. a remote screening device (900), capable of communicating with a server over a communications network, the remote screening device comprising:
      i. an imaging device (910) capable of scanning a tissue sample, the imaging device (910) configured to determine a periodic time interval (918) and generate imaging frames (912) of a tissue sample (913) within the periodic time interval (918), wherein the imaging frames comprise a scan across the tissue sample;
      ii. a camera (911) disposed to observe the area of the tissue sample (913) being scanned by the imaging device, the camera (911) capable of generating a camera image (915) of the tissue sample, wherein the camera image comprises a reference frame;
      iii. an output device; and
      iv. a device processor (930), operationally connected to the imaging device (910), the camera (911) and the output device, wherein the device processor (930) is configured to execute computer-readable instructions comprising:
         A. receiving the imaging frames (912) from the imaging device (910);
         B. receiving a camera image (915) from the camera;
         C. identifying the location (914) of the imaging frames within the reference frame of the camera image (915);
         D. pre-processing the image frames (912) to prepare them for classification;
         E. using a supervised learning algorithm (940) to classify the image frames (912) within a plurality of classifications, wherein the supervised learning algorithm of the server (932) is identical to the supervised learning algorithm of the screening device (900), wherein the supervised learning algorithm takes as inputs the locations of the imaging frames within the reference frame of the camera image, and the imaging frames, and produces as an output a classification (946), wherein the supervised learning algorithm (940) uses a plurality of parameters (941) to compute the classification (946); and
         F. reporting a classification (946) to a user using the output device;
         G. receiving updated parameters from a server (932);
      wherein within the periodic time interval determined by the imaging device (910), the device processor (930) is capable of generating the classification (946) after generating the imaging frames (912) by the imaging device (910);
   b. the server (932) capable of communicating with the remote device (900) via a communications network (933), the server (932) comprising:
      i. a memory, capable of storing:
         A. computer readable instructions;
         B. a set of training data (942) comprising a plurality of sets of sample images (943) of tissue samples (913), the locations of the sample images relative to others in the same set, and predetermined classifications (946), wherein each set of sample images comprises a set of images of a single tissue sample; and
         C. a plurality of parameters (941); and
      ii. an input mechanism, comprising means for a user to upload additional sets of images to the server;
      iii. a server processor (936), configured to execute computer readable instructions comprising:
         A. training the supervised learning algorithm (940) using the training data set (942) to classify images of tissue samples (912), wherein training comprises adjusting the plurality of parameters (941) so as to minimize a cost function, wherein the cost function is a function of the number of incorrect classifications output by the algorithm for a subset of the training data set;
         B. receiving sets of images (912) from the input mechanism, their locations within a common reference frame, and classifications (946);
         C. adding the received sets of images (912), locations, and classifications (946) to the training data set (942);
         D. updating the training of the supervised learning algorithm (940), comprising updating the plurality of parameters (941); and
         E. transmitting the updated plurality of parameters (941) to the remote device (900).

8. The system of claim 7, wherein the classifications (946) comprise a healthy class and a malignant class.

9. The system of claim 7, wherein the supervised learning algorithm (940) is a deep neural network (944).

10. The system of claim 7, wherein the periodic time interval (918) of the imaging device (910), and the time the device processor (930) takes to classify the image (912) at each time interval, is one second or less.

11. The system of claim 7, wherein the device and server processors comprise at least one multi-core processors such as a graphic processing unit (GPU).

12. The system of claim 7, wherein the training data set is constructed by determining a classification for a subset of imaging frames in a scan and extrapolating the classification to nearby imaging frames in the same set.

13. The system of claim 7, wherein pre-processing the image frame (912) to prepare it for classification comprises:
   a. determining an edge (913) of the image (912);
   b. flattening the image (912) based on the edge (913);
   c. normalizing and scaling the intensity of the image;
   d. selecting a region of interest (ROI) (914) of the flattened image (912); and
   e. generating a depth resolved intensity distribution (916) of the ROI (914).

14. The system of claim 7, wherein the server (932) is implemented in a cloud computing architecture.

15. The system of claim 7, wherein the imaging device (910) is an optical coherence tomography device, comprising:
   a. an optical imaging light source (202);
   b. a beam splitter (203);
   c. a fiber optic collimator (128) configured to collimate a light beam from the source (202);
   d. a gradient refractive index (GRIN) rod lens (118), capable of reflecting light outwards from the probe into surrounding tissue, optically connected to the fiber optic collimator (128), wherein the collimated light beam from the fiber optic collimator is directed into the GRIN rod lens; and
   e. a detector, optically connected to the gradient refractive index rod lens and to the optical imaging light source, capable of generating optical coherence tomography (OCT) images via interferometry.

16. The system of claim 7, wherein the imaging device is an auto-fluorescence imaging device, a confocal microscopy device, a narrow band imaging (NBI) device, or a Raman spectroscopy device.

17. The system of claim 15, further comprising a set of galvanic mirrors (106, 108), disposed to direct light from the collimator into the GRIN rod lens.

18. The system of claim 15, further comprising a beam reduction relay optics (114) configured to reduce a diameter of the light beam from the set of galvanic mirrors (106, 108) into an objective lens (116), the objective lens configured to focus the light beam into the GRIN rod lens (118), wherein the set of galvanic mirrors (106, 108) includes an X-axis galvanic mirror (106) configured to scan the light beam in a longitudinal direction and further includes a Y-axis galvanic mirror (108) configured to scan the light beam in a transverse direction.

19. The system of claim 15, wherein the device further comprises a fine needle aspiration biopsy needle (1003).

20. The system of claim 7, wherein the imaging device is an optical coherence tomography device, comprising:
   an optical imaging light source (202);
   b. a beam splitter;
   c. a fiber optic collimator (128) configured to collimate light from the source (202);
   d. a fiber optic rotary joint (414) operative coupled to a fiber (418), the fiber optic rotary joint configured to rotate the fiber (418) inside the tissue;
   e. the fiber, having an angle cleaved portion, capable of focusing and directing light into the surrounding tissue; and
   f. a detector, optically connected to the light source and the fiber.

* * * * *